US012670992B2

(12) United States Patent
    Habboushe et al.

(10) Patent No.: US 12,670,992 B2
(45) Date of Patent: Jun. 30, 2026

(54) COMPUTERIZED SYSTEM TO PROVIDE MEDICAL DIAGNOSIS, PROGNOSIS, AND TREATMENT USING MORE REFINED DIGITAL HEALTH RECORDS HAVING IMPROVED CONTEXT

(71) Applicant: MD Aware LLC, New York, NY (US)

(72) Inventors: Joseph Habboushe, New York, NY (US); Graham Walker, San Francisco, CA (US)

(73) Assignee: MD Aware LLC, New York, NY (US)

( * ) Notice: Subject to any disclaimer, the term of this patent is extended or adjusted under 35 U.S.C. 154(b) by 89 days.

(21) Appl. No.: 18/787,719

(22) Filed: Jul. 29, 2024

(65) Prior Publication Data

US 2024/0387048 A1     Nov. 21, 2024

Related U.S. Application Data

(63) Continuation-in-part of application No. 17/102,328, filed on Nov. 23, 2020, now abandoned, which is a continuation-in-part of application No. 15/416,831, filed on Jan. 26, 2017, now abandoned.

(60) Provisional application No. 62/289,831, filed on Feb. 1, 2016.

(51) Int. Cl.
    *G16H 50/20*      (2018.01)
    *G06F 40/166*     (2020.01)
    *G16H 10/60*      (2018.01)

(52) U.S. Cl.
    CPC ........... *G16H 50/20* (2018.01); *G06F 40/166* (2020.01); *G16H 10/60* (2018.01)

(58) Field of Classification Search
    CPC .................................................. G16H 50/20
    See application file for complete search history.

(56) References Cited

U.S. PATENT DOCUMENTS

2014/0278448 A1*    9/2014    Sadeghi ................. G06Q 10/10
                                                             705/2
2018/0174311 A1*    6/2018    Kluckner ............... G06V 10/25

* cited by examiner

*Primary Examiner* — Jason B Dunham
*Assistant Examiner* — Huma Waseem
(74) *Attorney, Agent, or Firm* — Sheppard Mullin Richter & Hampton LLP

(57)                    ABSTRACT

A method of improving diagnosis, prognosis, or treatment includes accessing a digital health record, identifying, from the digital health record, an entry in which a replacement string or an additional string is to be suggested, determining a particular string to suggest as a replacement or addition to existing text in the entry, in response to suggesting the particular string, presenting a source of the particular string and one or more alternatives to the particular string, receiving an input indicating whether the particular string or the one or more alternatives are accepted, updating the entry based on the received input, and determining a medical diagnosis, prognosis, or treatment according to the updated entry. This method may provide diagnosis, prognosis, or treatment for COVID-19 patients.

20 Claims, 23 Drawing Sheets

200

Patient Data — 204

202

| | Date | Value | |
|---|---|---|---|
| Temperature | 9/1/2019 | 99 | Chief Complaint Headaches and back pain after MVA |
| BP Systolic | 9/1/2019 | 122 | History of Present Illness (HPI) 21 year old single female complaints of dull headache for 4 weeks. Possible history of hypertension?   206 |
| BP Diastolic | 9/1/2019 | 84 | |
| Pulse Rate | 9/1/2019 | 66 | |
| Pulse Rhythm | 9/1/2019 | regular | |
| Resp Rate | 9/1/2019 | 12 | Review of Systems (ROS) No rash, bruising, change in color, hair loss, lymph node enlargement, or joint pain reported, rapid breathing   208 |
| Weight | 9/1/2019 | 153 | |
| Height | 9/1/2019 | 67 | |
| Auscul Heart | 9/1/2019 | normal | |
| Sodium | 9/1/2019 | 141 | Past Medical History Treated for concussion 8/2/2017; diabetic   210 |
| Potassium | 9/1/2019 | 4.7 | |
| Chloride | 9/1/2019 | 101 | Social History No smoking, no drugs, social drinker, plays college soccer   212 |
| $CO_2$ | 9/1/2019 | 23 | |
| Calcium | 9/1/2019 | 9.3 | Family History Mother/father have back problems, hypertension   214 |
| Cholesterol | 9/1/2019 | 190 | |
| HDL | 9/1/2019 | 60 | |

Medications List — 216
1) Motrin Migrane Pain 200mg orally, 1 tab to 4 tabs
2) Celebrex, 1 tab
3) Lisinopril, 1 tab
4) Chlorthalidone, 1 tab

Problems List — 218
Headache, postconcussion syndrome, dizziness, poor concentration, possible loss of consciousness

Diagnosis — 220
Concussion; possible back strain; spinal injury

Current Plan — 222
Bracing, or stabilization of back

Testing Results

Blood Test 9/1/2019
17:30:00 EST

| | Date | Value | | Standard Range |
|---|---|---|---|---|
| RBC (M/μL) | 9/1/2019 | | 5.1 | 4.7 - 6.1 |
| WBC | 9/1/2019 | | 6.3 | 4.5 - 11 |
| Hgb | 9/1/2019 | | 14 | 12 - 16 |
| Hct | 9/1/2019 | | 39 | 37 - 47 % |
| MCV | 9/1/2019 | | 15 | 14 - 18 |
| MCH (pg) | 9/1/2019 | | 27 | 27 - 35 |
| MCHC | 9/1/2019 | | 28% | 31 - 37% |
| Neutrophils | 9/1/2019 | | 62% | 50 - 81% |
| Bands | 9/1/2019 | | 1% | 1 - 5% |
| Lymphocytes | 9/1/2019 | | 15% | 14 - 44% |
| Monocytes | 9/1/2019 | | 2% | 2 - 6% |
| Eosinophils | 9/1/2019 | | 1% | 1 - 5% |
| Basophils | 9/1/2019 | | 0.40% | 0 - 1% |

MRI 9/1/2019
16:30:00 EST

252

254

Patient Data

| | Date | Value |
|---|---|---|
| Temperature | 9/1/2019 | 99 |
| BP Systolic | 9/1/2019 | 122 |
| BP Diastolic | 9/1/2019 | 84 |
| Pulse Rate | 9/1/2019 | 66 |
| Pulse Rhythm | 9/1/2019 | regular |
| Resp Rate | 9/1/2019 | 12 |
| Weight | 9/1/2019 | 153 |
| Height | 9/1/2019 | 67 |
| Auscul Heart | 9/1/2019 | normal |
| Sodium | 9/1/2019 | 141 |
| Potassium | 9/1/2019 | 4.7 |
| Chloride | 9/1/2019 | 101 |
| $CO_2$ | 9/1/2019 | 23 |
| Calcium | 9/1/2019 | 9.3 |
| Cholesterol | 9/1/2019 | 190 |
| HDL | 9/1/2019 | 60 |

720

710

202

ROS

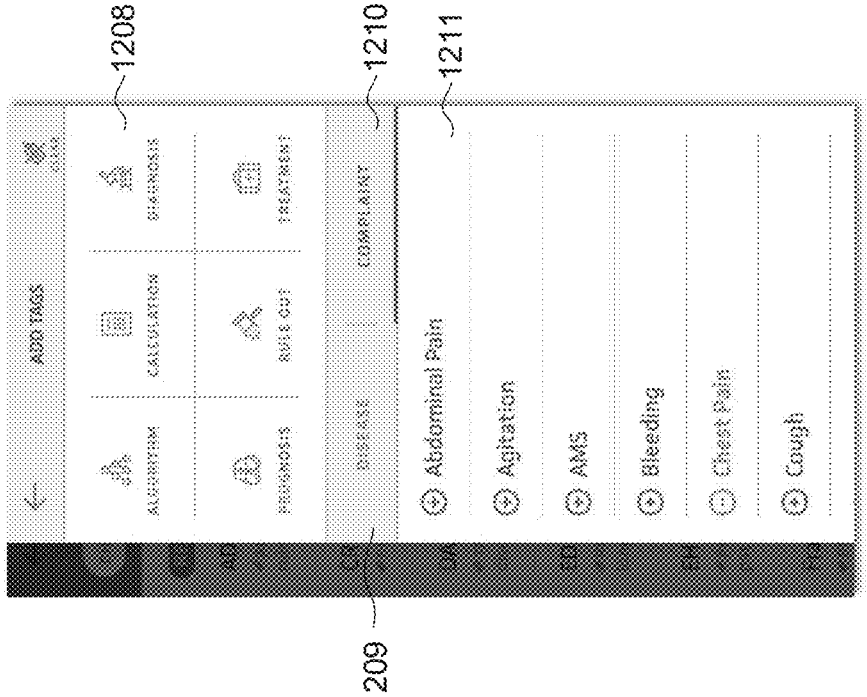

ADD TAGS

ALLERGIES    CALCULATION    RULE OUT    SOCK ALERT

DIAGNOSIS    TREATMENT    COMMON ALERT

- Abdominal Pain
- Agitation
- AMS
- Bleeding
- Chest Pain
- Cough

1107

CHEST PAIN

ADAPT Protocol
*A sensitive, rule out diagnostic 2-hour rule out for low risk chest pain.*

CRUSADE Score
*Assesses bleeding risk after NSTEMI.*

DASH Score
*Assesses suspected. Guides in discontinue anticoagulation in VTE.*

EDACS
*Risk tool identifies low risk chest pain, longer but more specific than HEART.*

EHMRG Score
*Assesses Mortality of emergency CHF patients.*

Framingham Risk Score
*Assesses Risk of MI in 10 years.*

FIGURE 11

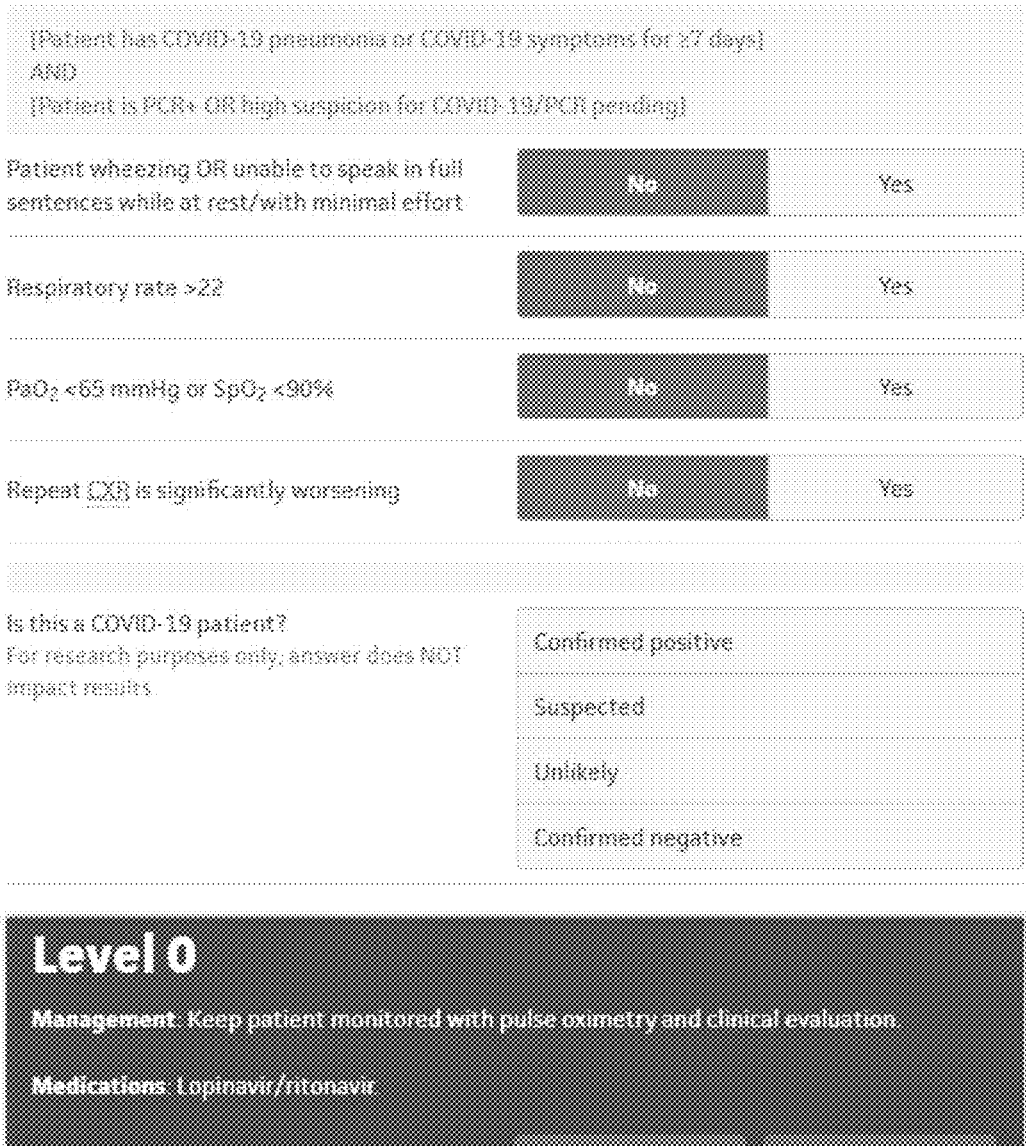

- In Italy, this score is being used in patients who have COVID-19 pneumonia OR have had COVID-19 symptoms for ≥7 days AND are either PCR+ OR high clinical suspicion for COVID-19.
- This is used for every single patient with these diagnoses, and is critical in the hospital in Brescia, Italy where it was developed to compare and quickly summarize a patient's clinical severity during this pandemic.

[Patient has COVID-19 pneumonia or COVID-19 symptoms for ≥7 days]
AND
[Patient is PCR+ OR high suspicion for COVID-19/PCR pending]

Patient wheezing OR unable to speak in full sentences while at rest/with minimal effort — No / Yes Respiratory rate >22 — No / Yes PaO₂ <65 mmHg or SpO₂ <90% — No / Yes Repeat CXR is significantly worsening — No / Yes Is this a COVID-19 patient?
For research purposes only, answer does NOT impact results Confirmed positive Suspected Unlikely Confirmed negative

Level 0

Management: Keep patient monitored with pulse oximetry and clinical evaluation

Medications: Lopinavir/ritonavir

Copy Results    Next Steps

FIGURE 20

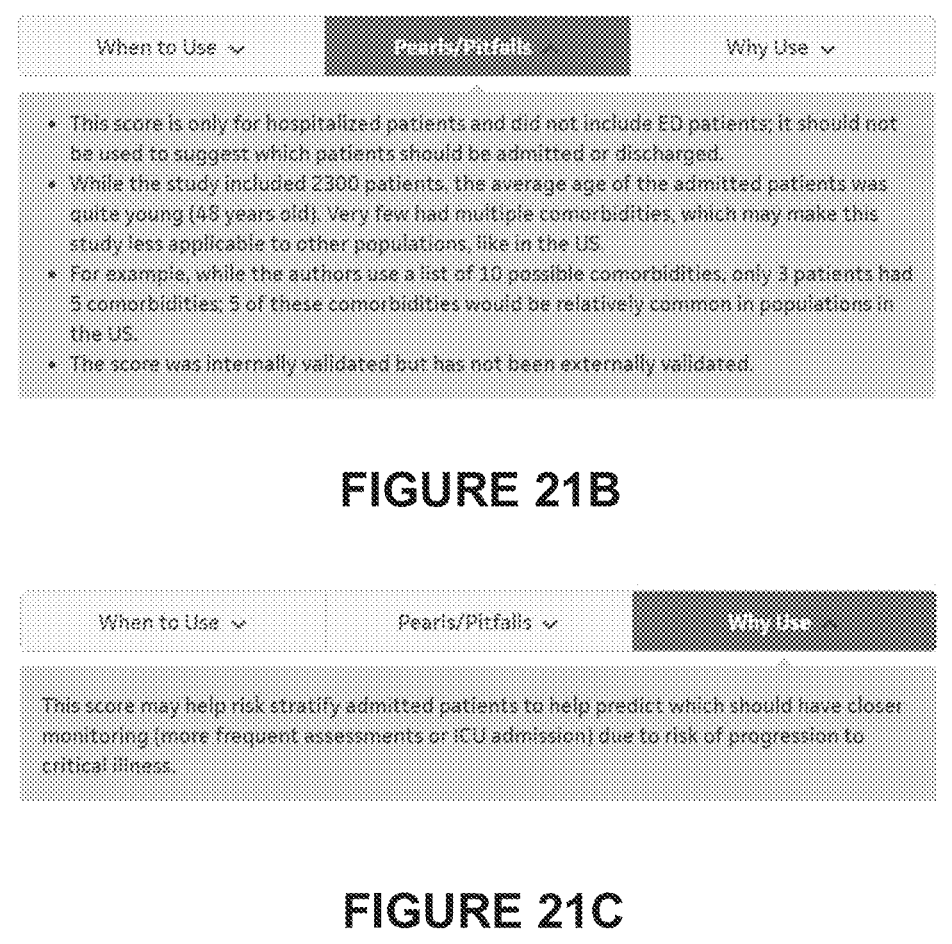

| When to Use ⌄ | Pearls/Pitfalls | Why Use ⌄ |
|---|---|---|

- This score is only for hospitalized patients and did not include ED patients. It should not be used to suggest which patients should be admitted or discharged.
- While the study included 2300 patients, the average age of the admitted patients was quite young (48 years old). Very few had multiple comorbidities, which may make this study less applicable to other populations, like in the US.
- For example, while the authors use a list of 10 possible comorbidities, only 3 patients had 5 comorbidities. 5 of these comorbidities would be relatively common in populations in the US.
- The score was internally validated but has not been externally validated.

FIGURE 21B

| When to Use ⌄ | Pearls/Pitfalls ⌄ | Why Use |
|---|---|---|

This score may help risk stratify admitted patients to help predict which should have closer monitoring (more frequent assessments or ICU admission) due to risk of progression to critical illness.

FIGURE 21C

Consider applying the qCSI to risk-stratify COVID-19 patients who are being admitted to the hospital. The derivation study used data up to 4 hours into the ED course. Patients with greater than 6L O₂ requirement at any time in the ED were excluded. The score has not been validated as a discharge tool.

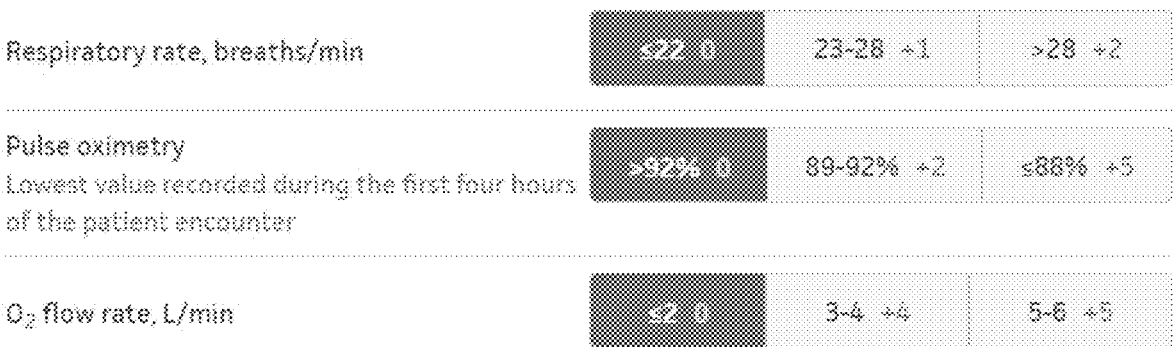

Respiratory rate, breaths/min

| <22 0 | 23-28 +1 | >28 +2 |

Pulse oximetry
Lowest value recorded during the first four hours of the patient encounter

| >92% 0 | 89-92% +2 | ≤88% +5 |

O₂ flow rate, L/min

| ≤2 0 | 3-4 +4 | 5-6 +5 |

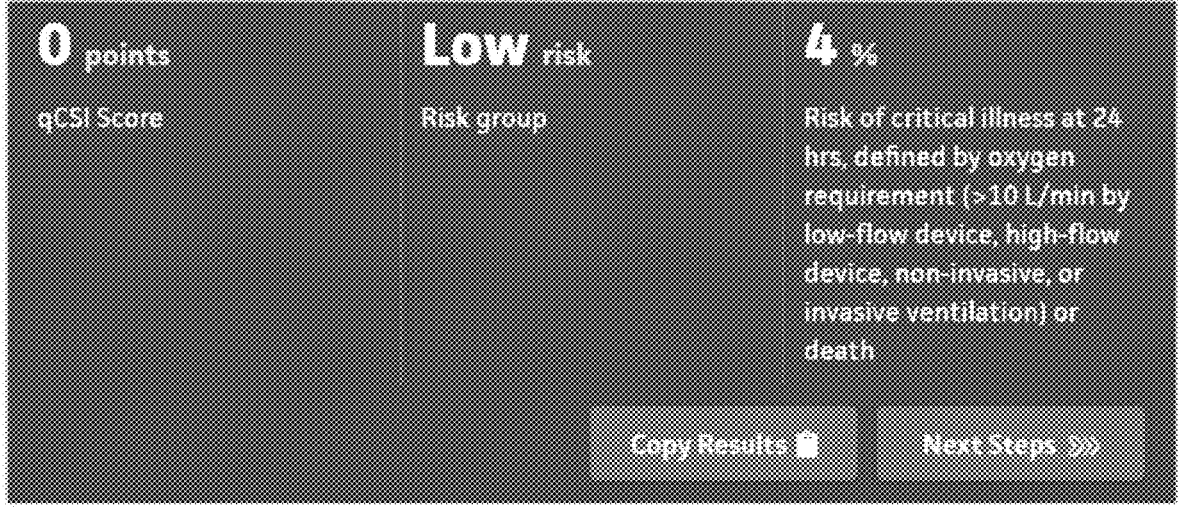

0 points          Low risk          4 % qCSI Score          Risk group          Risk of critical illness at 24 hrs, defined by oxygen requirement (>10 L/min by low-flow device, high-flow device, non-invasive, or invasive ventilation) or death Copy Results          Next Steps

FIGURE 22

COMPUTERIZED SYSTEM TO PROVIDE MEDICAL DIAGNOSIS, PROGNOSIS, AND TREATMENT USING MORE REFINED DIGITAL HEALTH RECORDS HAVING IMPROVED CONTEXT

CROSS REFERENCE TO RELATED APPLICATIONS

This application is a continuation-in-part under 35 U.S.C. § 120 of U.S. patent application Ser. No. 17/102,328, filed Nov. 23, 2020, which is a continuation-in-part under 35 U.S.C. § 120 of U.S. patent application Ser. No. 15/416,831, filed Jan. 26, 2017, now abandoned, which claims the benefit under 35 U.S.C. § 119 (e) of U.S. Provisional Patent Application No. 62/289,831, filed Feb. 1, 2016, the disclosure of which are hereby incorporated by reference, in their entireties, for all purposes.

BACKGROUND

Digital records of patient health, such as electronic health records (EHRs) and electronic medical records (EMRs), are recorded by medical professionals to document patient data which may include diagnoses, medications, immunizations, and family medical histories. In their busy schedules, medical professionals have limited time to update the digital records. To expedite the entry of the digital records, medical professionals may utilize abbreviations, acronyms, or other shortcuts to save time. However, such entries may be ambiguous or incomplete to other viewers of the digital records, such as other medical professionals or patients. These ambiguous or incomplete entries may be catalysts that could lead to downstream consequences such as incorrect prescriptions or improper diagnosis, prognosis, or treatment. Incorrect prescriptions in the United States alone result in death of an estimated 7,000 to 9,000 people per year. Thus, the necessity of accurate, clear, and complete digital records cannot be overstated.

SUMMARY

The present disclosure provides systems and methods that assist medical professionals, healthcare providers, patients or other individuals (generally referred to as "users") to increase accuracy and completeness of data records of patient health and improve diagnosis, prognosis or treatment of patients.

Described herein, in some embodiments, is a method of improving medical diagnosis, prognosis, or treatment, comprising: accessing a digital health record, wherein the digital health record comprises windows corresponding to different categories of information; identifying, from the digital health record, an entry in which a replacement string or an additional string is to be suggested, based on an ambiguity of the entry or an inconsistency or a conflict with other data in the digital health record; obtaining a first training set that comprises first suggestions that are accepted as being viable replacements or additions to the existing text; obtaining a second training set that comprises second suggestions that are rejected as being nonviable replacements or additions to the existing text; training the machine learning model using the first training set and the second training set; predicting, by the one or more machine learning models, a particular string to suggest as a replacement or addition to existing text in the entry and one or more alternatives to the particular string based on respective probabilities of veracity of the particular string and the one or more alternatives; in response to suggesting the particular string, presenting sources of data within the digital health record that supports the particular string and the one or more alternatives to the particular string, wherein the sources of data correspond to one or more of the windows; receiving an input, the input indicating whether the particular string or the one or more alternatives are accepted, or including a manually inputted string that is distinct from the particular string and the one or more alternatives; updating the entry based on the received input; determining or inferring any particular emphasis or any particular bias of the input towards a particular window of the digital health record over other windows of the digital health record; training the machine learning model by adjusting any one or more weights attributed to the particular portion of the digital health record according to the any particular emphasis or any particular bias; determining a medical procedure according to the updated entry; transmitting, to a device associated with the medical procedure, a signal to activate the device and any protocol associated with the medical procedure; following the execution of the protocol by the device, receiving, from the device, a result associated with the medical procedure; updating a portion of the digital health record according to the result; determining a presence of a particular medical condition based on semantic segmentation and instance segmentation to determine first boundaries between different tissue types and second boundaries between common tissue types; determining or inferring that the particular medical condition comprises a fracture; determining an absence of a reference to a surgery within the windows, wherein the determining of the medical procedure comprises determining that the surgery is to be implemented, the machine learning model being trained according to particular medical conditions and particular measures to be implemented; presenting, as an overlay over an existing window or a sidebar at a side of the existing window, a suggestion of a surgery; receiving an acceptance of the suggestion of the surgery, wherein the device comprises a surgical machine; presenting a prompt to select a surgical machine; and receiving an acceptance of the surgical machine.

In some embodiments, the machine learning model, which was trained using the first training set and the second training set, is also trained or otherwise configured to perform instance segmentation and semantic segmentation.

The method may be carried out by one or more processors having a combination of software, hardware, and/or firmware. For example, the method may be carried out by one or more application specific integrated circuits (ASICs). The one or more ASICs may include a plurality of neurons and/or a plurality of synaptic circuits, in which at least a subset of the neurons may be connected via one of the plurality of synaptic circuits.

In some embodiments, the determining a particular string to suggest comprises determining a particular string indicating a COVID-19 status of a patient, the COVID-19 status being determined based on whether a patient has breathing or speech difficulties, a respiratory rate, a $PaO_2$ and $SpO_2$ level, and an analysis of a chest X-ray of the patient.

In some embodiments, the method comprises receiving a textual input into the entry. In some embodiments, the determining the particular string to suggest is simultaneous with the receiving of the textual input.

In some embodiments, the determining the particular string is based on a context of the entry.

In some embodiments, the digital health record comprises a problem list including one or more illnesses, one or more injuries, and one or more risk factors and a medication list including one or more drugs and one or more prescribed respective dosages. In some embodiments, the determining the particular string is based on an item in the problem list and an item in the medication list. In some embodiments, the method further comprises generating the problem list and the medication list.

In some embodiments, the method further comprises identifying other entries in the digital health record to be updated based on the input.

In some embodiments, the presenting one or more alternatives to the particular string is in a drop-down list that enables switching between selection of the particular string or the one or more alternatives.

In some embodiments, the method further comprises presenting a confidence level indicating a probability or degree of reliability or relevance of the particular string.

In some embodiments, the method further comprises presenting confidence levels indicating one or more probabilities or degrees of reliability or relevance of each of the one or more alternatives.

In some embodiments, the determining a particular string comprises importing a determination of a parameter.

In some embodiments, the particular string comprises a dot-phrase or a native macro. In some embodiments, the input indicates that the particular string is accepted. In some embodiments, the method further comprises populating a chart based on the input.

In some embodiments, in response to receiving the input to override the particular string and the one or more alternatives, the entry is maintained.

In some embodiments, the identifying an entry in which a replacement string or an additional string is to be suggested comprises identifying a numeral that is missing a subsequent unit of measurement.

In some embodiments, the method further comprises flagging the numeral that is missing a subsequent unit of measurement.

In some embodiments, the determining a particular string to suggest comprises determining a particular unit of measurement to append to the numeral based on the context of the entry.

In some embodiments, the method further comprises identifying a type of the received input. In some embodiments, the determining a particular string to suggest is based on a machine learning model trained by a feedback mechanism taking into account the type of the received input.

In some embodiments, the method further comprises identifying a frequency at which the received input or the one or more alternatives is selected; and wherein the determining a particular string to suggest is based on a machine learning model trained by a feedback mechanism taking into account the type of the received input.

In some embodiments, the method further comprises identifying data in the entry having a reliability below a threshold; and flagging the data.

In some embodiments, the identifying data in the entry having a reliability below a threshold comprises detecting data having a source other than a sensor reading or a calculation or determination of a parameter.

In some embodiments, the method further comprises presenting one or more respective sources of the one or more alternatives to the particular string.

In some embodiments, the method further comprises, in response to receiving the input, determining, based on the received input, whether an additional test is to be conducted.

In some embodiments, the method further comprises suggesting a deletion of a portion of the existing text in the entry.

In some embodiments, the method further comprises identifying a plurality of entries of which at least one of the entries conflicts or contradicts other entries; and determining which of the entries is more likely to be inaccurate.

Various embodiments of the present disclosure provide a device, one or more processors, and/or non-transitory storage medium to implement the method as described above. For example, the device may include system having one or more processors and a memory storing instructions that, when executed by the one or more processors, cause the system to perform the method as described above.

These and other features of the devices, methods, and non-transitory computer readable media disclosed herein, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for purposes of illustration and description only and are not intended as a definition of the limits of the invention.

BRIEF DESCRIPTION OF THE DRAWINGS

Certain features of various embodiments of the present technology are set forth with particularity in the appended claims. A better understanding of the features and advantages of the technology will be obtained by reference to the following detailed description that sets forth illustrative embodiments, in which the principles of the invention are utilized, and the accompanying drawings of which:

FIGS. 2A-2B illustrate exemplary implementations of a digital health data platform, in accordance with an embodiment.

FIGS. 9-15, 16A-16C, 17-20, 21A-21C, and 22 illustrate exemplary implementations of diagnostic tests, methods, or protocols, prognostic methods, algorithms, and/or determinations of treatment options, which may be implemented in conjunction with any of the implementations of the previous FIGS. 1-8. In particular, FIGS. 20, 21A-21C, and 22 are specific to COVID-19.

DETAILED DESCRIPTION

Embodiments described in this application provide a method, implemented by a system having one or more computer processors, that enhances an accuracy, reliability, and completeness of digital health records of patients, while seamlessly completing and/or transmitting electronic prescriptions, and synchronizing with diagnostic and surgical equipment. The system may detect entries in the digital health records that have potentially ambiguous, inaccurate, or unreliable data, and provide suggestions such as clinical concepts to rectify such data. The system may further present alternative suggestions, receive an input of which, if any, suggestion has been accepted or adopted, and incorporate whichever suggestion has been accepted or adopted into the digital health records. The system may include a machine learning model that is trained over time to improve the suggestions so that the suggestions include more accurate, relevant or appropriate data and/or more closely account for conventions of a particular medical practice. Additionally, once the system receives updated data, the system may automatically and dynamically update other relevant entries of the digital health data platform so that a practitioner does not need to manually search for each entry that needs to be updated. In summary, the system provides options or suggestions to revise incorrect or ambiguous data that would otherwise remain unchecked and automatically update entries in digital health records that may otherwise be forgotten, while coordinating and initiating diagnostic, prognostic, and treatment options.

In some embodiments, the system may be configured to determine a diagnosis, prognosis, or treatment of a patient actually or potentially infected by COVID-19 and/or indicate a severity of risk of such a patient. The system may determine one or more tests, protocols, or methods is/are most appropriate based on data of the patient provided in the digital health data platform.

Figure 1:
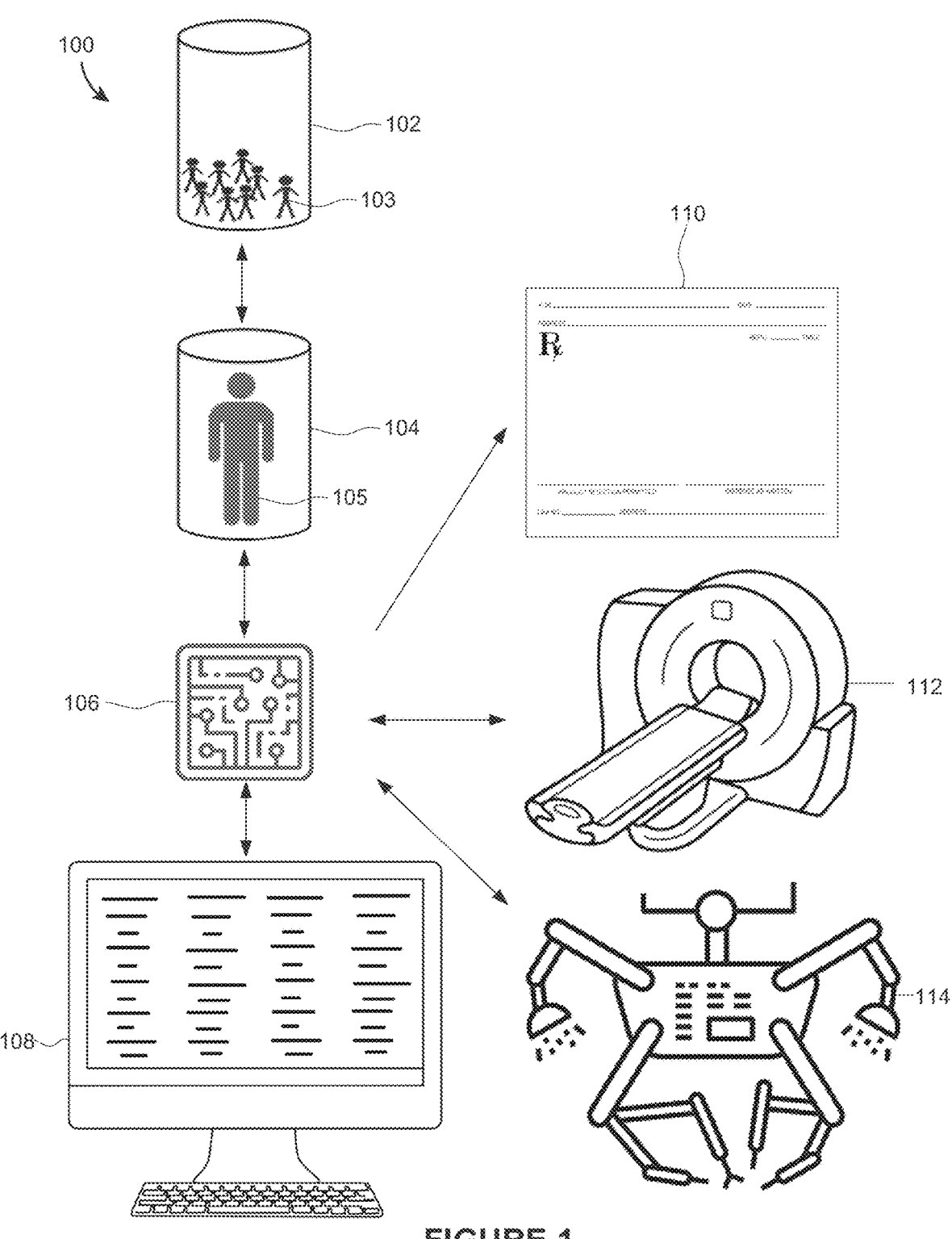
FIG. 1 illustrates an exemplary flow diagram of an improved medical diagnostic and treatment system, in accordance with an embodiment.

FIG. 1 illustrates an exemplary flow diagram of an improved medical diagnostic and treatment system. In FIG. 1, a database 102 may include medical data of patients 103. From the database 102, records 104 of a patient 105 may be selected, for example, on a device 108, by a user operating the device 108. The patient 105 may be a patient that is currently being operated on and/or a patient of interest, for example, of which further data is being gathered. One or more processors 106 may process and/or analyze the records 104, determine one or more suggestions to improve an accuracy, clarity, and/or completeness of the records 104 along with probabilities of relevance of each of the suggestions. In some embodiments, the suggestions may include terms as an addition, deletion, or replacement, based on a context of the records 104 of the patient 105, and/or of the patients 103 as a whole in the database 102. The one or more processors 106 may present, onto the device 108, suggestions and the probabilities of relevance. The one or more processors 106 may present the suggestions and the probabilities of relevance simultaneous with text being inputted, for example, on the device 108, or after text has been completely inputted. For example, text may be inputted by a user of the device 108. The device 108 may, in some embodiments, be a personal computer, a handheld device such as a mobile phone, tablet or any other device. The device 108 may receive an input regarding which, if any, suggestions have been adopted or accepted. The device 108 may transmit the input back to the one or more processors 106. The one or more processors 106 may update the records 104 of the patient 105 from the received input, thereby updating the database 102.

The one or more processors 106 may be trained to improve the suggestions and determination of probabilities of relevance based on which of the suggestions have been adopted or accepted. For example, if the input to the device 108 indicates that the suggestions weigh certain portions of the patient data, such as the problems list or the testing results, more heavily, the one or more processors 106 may be trained to determine and/or output suggestions that more heavily weigh those portions of the patient data. As another example, if the input to the device 108 indicates that the suggestions tend to have more definitive language, such as "concussion" as opposed to "possible concussion" or "probable concussion," the one or more processors 106 may be trained to determine and/or output suggestions that include more definitive language. In some embodiments, multiple training sets may be utilized to train the one or more processors, for example, a first training set may include instances in which one of the alternative suggestions has been accepted, and a second training set may include instances in which none of the alternative suggestions have been accepted.

The one or more processors 106 may further, upon receiving an input from the device 108 regarding a diagnosis, prognosis, or treatment, perform functions to improve the diagnosis or prognosis, and/or implement a treatment. For example, the one or more processors 106 may electronically record or fill out a prescription 110 and incorporate the prescription 110 into the records 104 of the patient 105, and to the database 102. In other examples, the one or more processors 106 may further communicate with an instrument by sending a signal to the instrument to further carry out a diagnosis, prognosis, or treatment. The instrument may be an imaging device such as a magnetic resonance imaging (MRI) machine 112 or a surgical machine 114. The one or more processors 106 may further transmit information about a protocol or program to be implemented at the instrument. The protocol or program may incorporate the input received from the device 108 at which suggestions were accepted or adopted. For example, if the input received from the device 108 was to add a MRI scan to a current plan, the one or more processors 106 may transmit to the MRI machine 112 a signal to active the MRI machine 112 and a program or protocol to be implemented. In such a manner, the one or more processors 106 can activate machines to further carry out a diagnosis, prognosis, or treatment. Further details of the operations of the one or more processors 106 are described below.

FIG. 2A illustrates an exemplary implementation of a digital health data platform, such as an EHR platform, depicting a panel 200 that includes a patient chart of the patient 105. The panel 200 may be implemented, in some embodiments, as the records 104 of the patient 105. In other words, the records 104 may be organized in a format of the panel 200. In FIG. 2A, the digital health data platform may include a clinical data window or section (hereinafter "window") 202, a chief complaint window 204, a history of present illness (HPI) window 206, a review of systems (ROS) window 208, a past medical history window 210, a social history window 212, a family history window 214, a medications list window 216, a problems list window 218, a diagnosis window 220, and a current plan window 222. The one or more processors 106 may determine and present suggestions in any of the aforementioned windows based on any of the records 104 of the patient 105, and/or information from any of the patients 103 in the database 102. The one or more processors 106 may accept an input of numbers and/or strings into any of the aforementioned windows either manually or a selection of numbers and/or strings via a drop-down list or a drop-down menu.

Figure 2B:
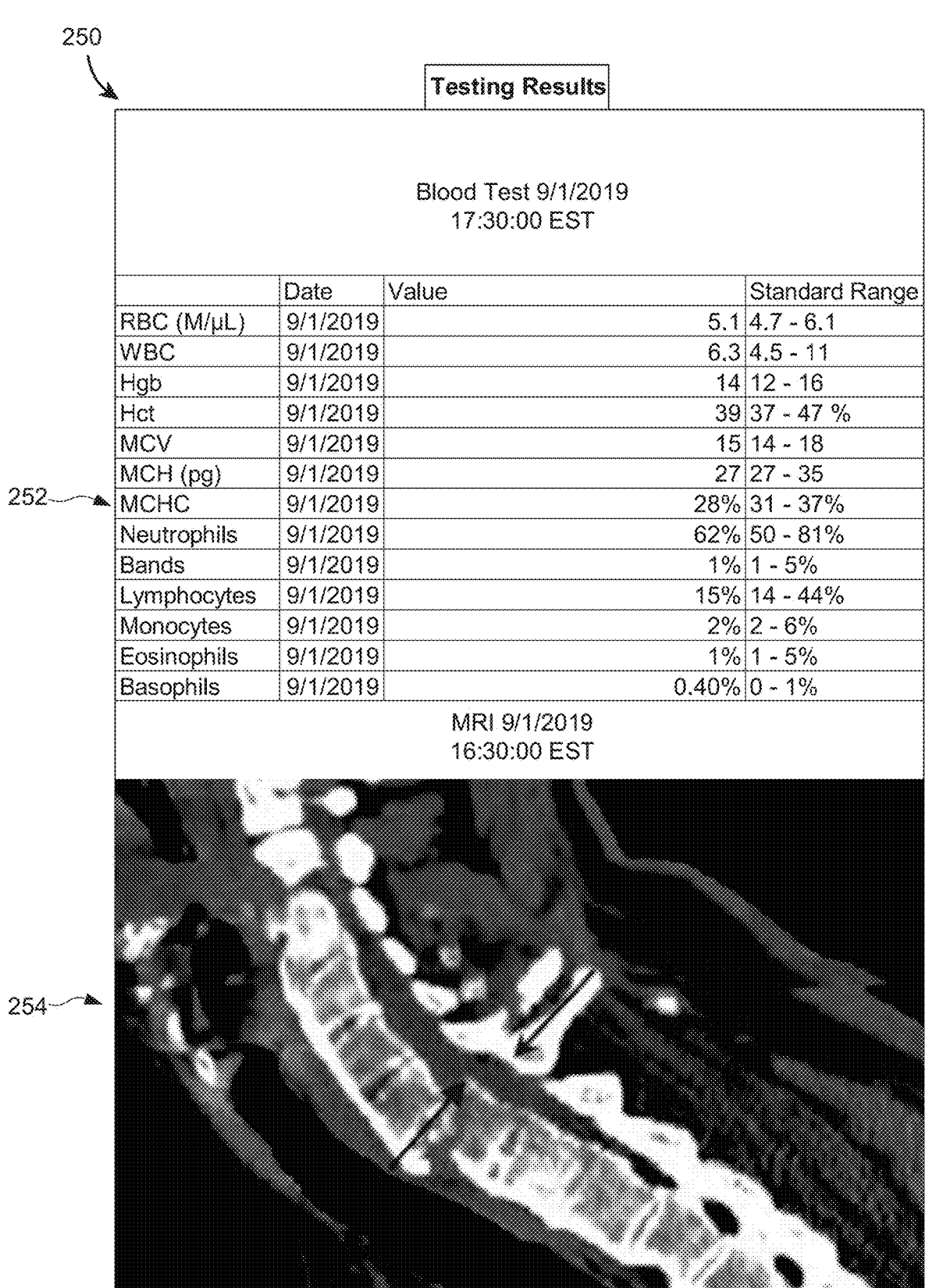

FIG. 2B illustrates an exemplary implementation of a digital health data platform, such as an EHR platform, depicting a panel 250 that includes testing results of the patient 105, which may include blood test data 252 and MRI data 254. In some examples, the MRI data 254 may have been obtained in response to, or after, the one or more processors 106 presented a suggestion to incorporate a MRI in a current plan of diagnosis, prognosis, or treatment of the patient 105. The one or more processors 106 may transmit a signal to the MRI machine 112 in order to initiate a MRI scan of a back of the patient 105. Once the MRI machine 112 receives the instructions including settings and/or protocol of the MRI scan from the one or more processors 106, the MRI machine 112 may conduct the MRI scan and transmit results of the MRI scan to the one or more processors 106. The one or more processors 106 may then insert the MRI results including images into the panel 250. Although particular examples of diseases or medical conditions are mentioned for the sake of illustration, the implementation of FIGS. 2A and 2B may apply to any disease or medical condition.

Figure 3:
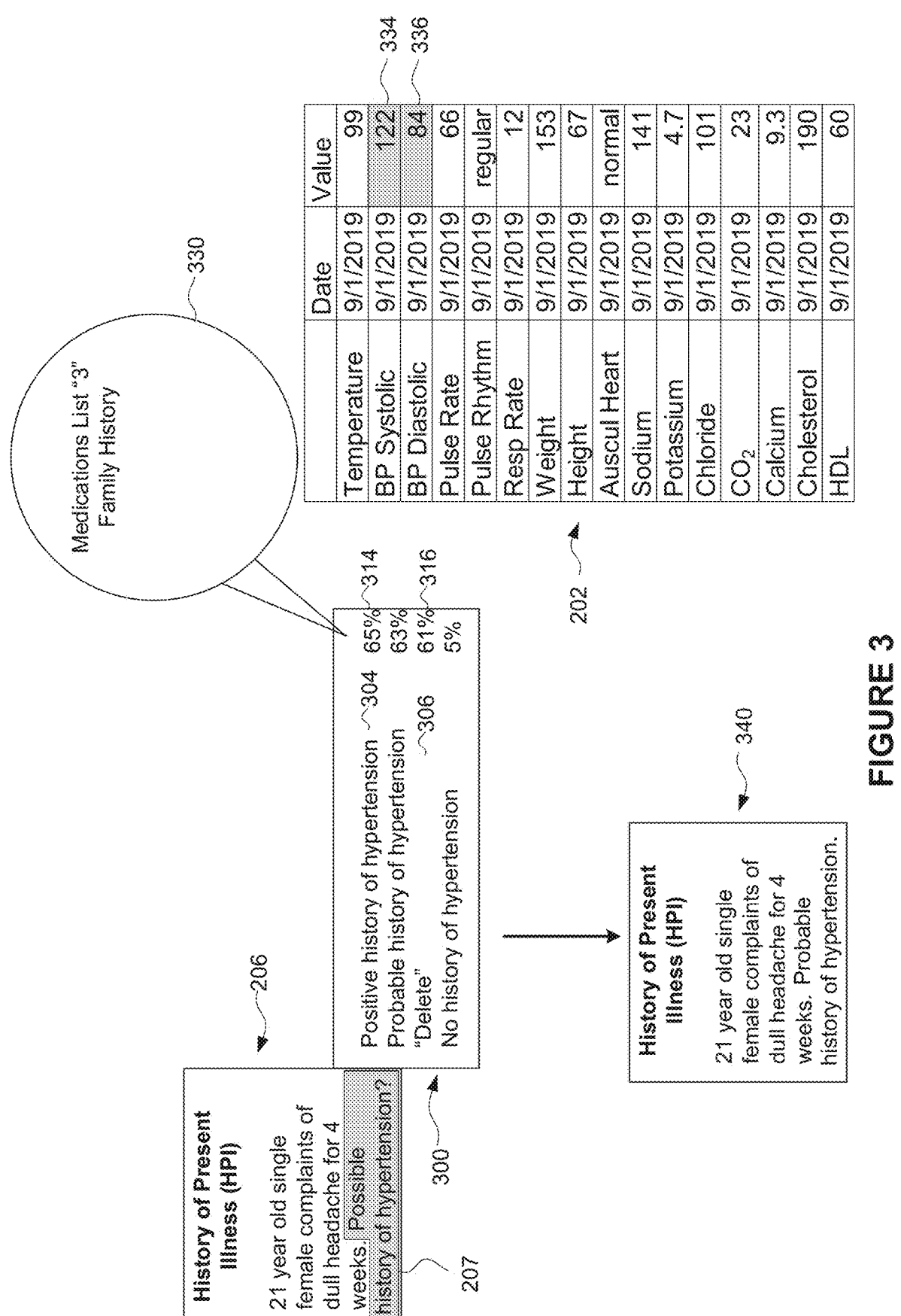
FIGS. 3-4, 5A-5B, and 6-8 illustrate exemplary implementations of mechanisms of updating the digital health data platform, in accordance with an embodiment.

FIG. 3 illustrates an exemplary implementation of a mechanism of updating the digital health data platform by the one or more processors 106, showing how the records 104 of the patient 105 are updated following suggestions, or options, presented by the one or more processors 106. As an example, the one or more processors 106 may determine and present a suggestion to modify any of the text in the panel 200. For example, the one or more processors 106 may recognize that text somewhere in the panel 200 may be ambiguous, inaccurate, or incomplete, and present replacement text to replace or add to the ambiguous, inaccurate, or incomplete text, and/or present an option to delete the ambiguous, inaccurate, or incomplete text. In some embodiments, the one or more processors 106 may only present replacement text if a probability of reliability of any of replacement text options or suggestions satisfies a certain threshold, such as 50%.

In FIG. 3, the one or more processors 106 may determine that text in the HPI window 206 may be ambiguous and may determine replacement text based on context from the records 104 of the patient 105 and/or other data in the database 102. In particular, the one or more processors 106 may determine that text 207, "Possible history of hypertension?" from the HPI window 206 may be ambiguous. In order to determine replacement text to suggest, the one or more processors 106 may extract other data from one or both of the panels 200 and 250, and/or other sources of data of the patient 105 or in the database 102 that is potentially relevant and/or related to text 207, "Possible history of hypertension?" For example, the extracted data may include data from the medications list window 216. Lisinopril, which is known to treat hypertension, being included in the medications list window 216 may be evidence to support that the patient 105 does indeed have a history of hypertension. In addition, the extracted data may include data from the family history window 214. Data in the family history window 214 indicates that both parents have hypertension, a further testament that the patient 105 has a history of hypertension. The extracted data may further include data from the patient chart 202, indicating that systolic and diastolic blood pressures of the patient 105 are within normal ranges. These blood pressure readings may support the possibility that the patient 105 does not have a history of hypertension.

Thus, the one or more processors 106 may have to balance potentially conflicting data from the panels 200 and 250 in order to determine replacement text to suggest and present to the device 108, in place of the text 207. Here, the one or more processors 106 may determine that the data from the medications list window 216 and the family history window 214 which suggest a history of hypertension outweigh the data from the patient chart 202, which suggests no history of hypertension.

Therefore, the one or more processors 106 may determine an option 304 to be, substituting, in place of the text 207, a replacement text option "Positive history of hypertension." The one or more processors 106 may further determine alternative options 306 which may include replacement text options "Probable history of hypertension," or "No history of hypertension." The one or more processors 106 may further determine that one of the alternative options 306 is to delete the text 207, "Possible history of hypertension," without substituting any text. The one or more processors 106 may further determine a probability of relevance of each of the replacement text or deletion options. The probability of relevance may indicate an extent to which each of the replacement text or deletion options is relevant and/or accurate. For example, a probability of relevance 314 of the option 304 may be determined to be 65%, indicating that some uncertainty exists as to whether the option 304 is relevant or accurate, in part because the patient chart 202 appears to suggest no hypertension. The alternative options 306 may have lower probabilities of relevance 316 compared to the probability of relevance 314 of the option 304.

The one or more processors 106 may present the option 304 and the alternative options 314 in a window 300 having a drop-down list or drop-down menu to enable a selection of an input from the device 108. The window 300 may provide a possibility of selecting any of the option 304 or the alternative options 314, or overriding all options. If the option 304 and the alternative options 314 have been overridden, other options include keeping the text 207 as is or manually inputting a different string to replace the text 207. Thus, the device 108 may indicate that none of the option 304 and the alternative options 314 are accepted or adopted. The window 300 may be implemented either as an overlay over existing medical data or in a sidebar to a side of the existing medical data, which may be presented in the panel 200 or 250. In FIG. 3, if the input from the device 108 indicates that the "Probable history of hypertension" option were selected, the one or more processors 106 may update, as an updated HPI window 340, the previous HPI window 206 having the text 207 replaced by, "Probable history of hypertension."

In some embodiments, the one or more processors 106 may present sources of data from any of the panels 200 or 250 from which the option 304 or the alternative options 314 were determined, inferred, or derived, as a tooltip, pop-out menu, popup window, or a hover box. As illustrated in FIG. 3, the one or more processors 106 may present a tooltip, pop-out menu, popup window, or a hover box 330 showing that the option 304 and the alternative options 314 were obtained from data in the medications list window 216, third item ("Lisinopril") and the family history window 214. The one or more processors 106 may additionally present an additional tooltip, pop-out menu, popup window, or a hover box showing sources of data that may introduce uncertainty of any of the option 304 and the alternative options 314 being reliable. In particular, the one or more processors 106 may highlight, as entries 334 and 336, data from the patient chart 202 that appears to lead away from a history of hypertension.

The one or more processors 106 may utilize machine learning, which may incorporate neural networks such as a convolutional neural network (CNN). In some examples, the machine learning model may be trained to detect ambiguous or erroneous entries using input training data that includes ambiguous or erroneous entries, which may conflict or not exactly be consistent with other data in a patient data platform. The machine learning model may be trained to recognize and output which particular entries are ambiguous or erroneous. Part of the training process may incorporate training data having inputs that appear primarily to support a particular clinical concept and outputs which may include any data sources that are conflicting or not exactly consistent with the clinical concept. The machine learning model may be trained to further determine possible replacement strings to replace the ambiguous or erroneous entries, using the same ambiguous or erroneous entries along with the other conflicting or inconsistent data as input and the possible replacement strings as an output. For example, the machine learning model may be trained to incorporate information from the conflicting or inconsistent data while formulating options of possible replacement strings. The inputs of training data may include medical data and the outputs may include a string that incorporates at least a portion of the medical data.

The machine learning model may further incorporate reinforcement learning to cope with the stochasticity in data entries in a patient data platform to improve the option 304 and the alternative options 314 over time. For example, the reinforcement learning may leverage a reward shaping mechanism which may further include Bayesian optimization, to modify algorithms of the one or more processors 106 over time based on input from the device 108 indicating a frequency at which the option 304 or the alternative options 314 are adopted or accepted, or overridden. In some embodiments, if the device 108 provides input that tends to override most of the presented options while changing the ambiguous or erroneous entries without incorporating any of the presented options, the one or more processors 106 may adapt by presenting options that conform more closely with a style and/or substance of information of the changed entries from the device 108. As an example, the device 108 may provide input that the text 207, "Possible history of hypertension?" should be changed to "Probable history of hypertension from medications list and family history" which does not conform to any of the option 304 or the alternative options 314. The one or more processors 106 may adapt by presenting future suggestions or options that also mention or include sources of information. The machine learning model, as will be elaborated on, may also perform segmentation such as instance and semantic segmentation, and/or be trained to perform instance and semantic segmentation.

In some examples, the one or more processors 106 may adapt by presenting or providing suggestions or options that take into account which types of options have been accepted by the device 108. For example, the one or more processors 106 may take into account that a selection from the device 108 is one of the alternative options 306, "Probable history of hypertension" rather than the option 304, "Positive history of hypertension," suggesting that less definitive language may be preferred. Thus, the one or more processors 106 may adapt by presenting options in the future that have less definitive language. The one or more processors 106 may also detect a type of language elsewhere in the panel 200 and conform to the detected type of language. In some examples, the one or more processors 106 may adapt by suggesting or presenting options that take into account relative weights to be attributed to each of the sources of data from any of the panels 200 and 250 in particular situations or in general. In the example shown in FIG. 3, the one or more processors 106 may infer that data from the medications list window 216 and the family history window 214 are to be weighted more heavily than data from the patient chart 202 in determining a history of hypertension. If additional selections from the device 108 indicate that data from the medications list window 216 and the family history window 214 are to be weighted more heavily than the patient chart 202 in other scenarios, the one or more processors 106 may accordingly weight data from the medications list window 216 and the family history window 214 more heavily while formulating its options or suggestions.

The probabilities of relevance 314 and 316 may also be adjusted based on input received from the device 108. For example, if input from the device 108 indicates that data from the medications list window 216 and the family history window 214 are to be weighted more heavily than other data at a high frequency, the probabilities of relevance of options or suggestions associated with or including such data may be adjusted to be higher. Although particular examples of diseases or medical conditions are mentioned for the sake of illustration, the implementation of FIG. 3 may apply to any disease or medical condition.

Figure 4:
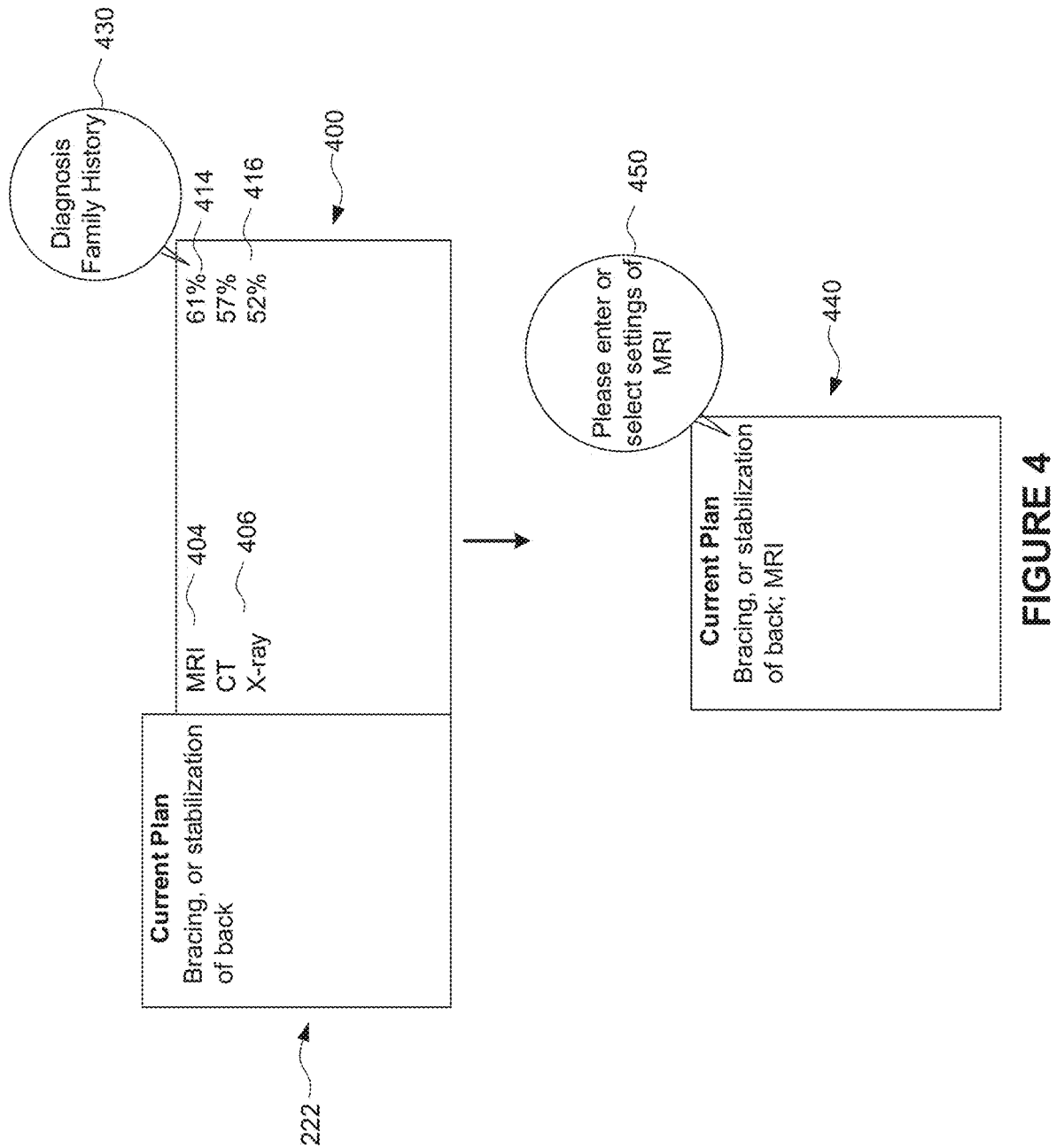

FIG. 4 illustrates an exemplary implementation of a mechanism of updating the digital health data platform by the one or more processors 106, showing how the records 104 of the patient 105 are updated following suggestions, or options, presented by the one or more processors 106. Relevant details provided with respect to other figures may also be applicable to the implementation shown in FIG. 4. In FIG. 4, the one or more processors 106 may provide options to further enrich an entry in the current plan window 222 by suggesting an option 404 of including a MRI scan, and alternative options 406 that include a CT scan or an X-ray instead. The one or more processors 106 may further present a probability of relevance 414 corresponding to the option 404 and probabilities of relevance 416 corresponding to the alternative options 406.

The one or more processors 106 may first recognize or determine that some type of imaging may be an appropriate further option to guide diagnosis, prognosis, or treatment, based on information presented in the chief complaint window 204. The one or more processors 106 may determine that no image has been recorded in the panel 250 corresponding to an applicable date such as a date indicated in the patient chart 202 of when the patient 105 was most recently seen in the clinic, and that no indication of an image has been recorded in the current plan window 222. To clarify, although the MRI data 254 is shown in the panel 250, the MRI data 254 may not have been present before the one or more processors 106 suggested an option 404 of including the MRI scan, and may only have been added afterwards. The one or more processors 106 may then determine which imaging options and/or modalities are most appropriate for a current problem, in this case, back pain.

The one or more processors 106 may present the option 404 and the alternative options 406 in a window 400 while further including a tooltip, pop-out menu, popup window, or a hover box 430 to provide a reasoning or justification for the option 404 and the alternative options 406. The window 400 may be implemented either as an overlay over existing medical data or in a sidebar to a side of the existing medical data, which may be presented in the panel 200 or 250. For example, the tooltip, pop-out menu, popup window, or the hover box 430 shows that data from the diagnosis window 220 and the family history window 214 indicates that the patient 205 has a back problem and that further diagnosis is required. The one or more processors 106 may then receive a selection from the device 108 regarding which, if any, of the option 404 or the alternative options 406 are adopted or accepted. In the example of FIG. 4, a selection from the device 108 indicates that the option 404 has been accepted.

The one or more processors may then output an updated current plan window 440 that includes the option 404, "MRI."

Subsequently, the one or more processors 106 may present, to the device 108, a prompt to select a protocol and/or settings of implementing an MRI scan. For example, the prompt may be in a form of a dialog 450. In some examples, the dialog 450 may be a pop-up window which enables a selection from predetermined settings or a manual entry from the device 108 of the protocol and/or settings to be followed. In some examples, the predetermined settings may include commonly used settings, such as settings commonly used in a diagnosis or prognosis of the current problem. In some examples, the dialog 450 may provide an option on the device 108 to select a commonly used setting while modifying specific parameters or properties of that setting. The one or more processors 106 may then communicate with an MRI machine (e.g., the MRI machine 112) and transmit the settings and/or protocol to be applied, to initialize the MRI machine 112.

The one or more processors 106 may be trained using training data having inputs of particular medical scenarios and outputs of what diagnostic or prognostic mechanisms are used in those particular medical scenarios. For example, the one or more processors 106 may be trained to recognize that MRI imaging is most commonly used in diagnosing back problems. In some examples, the one or more processors 106 may be trained to associate a reference to a back problem, for example, located somewhere in the panel 200 or 250, with an imaging modality. If the one or more processors 106 do not detect that any imaging modality is present in the panel 200 or 250, then the one or more processors 106 may determine that an option of an imaging modality should be, or is to be, presented at the device 108. However, if the one or more processors 106 do detect that an imaging modality is referred to on the applicable date somewhere in the panel 200 or 250, the one or more processors 106 may refrain from presenting an additional imaging modality, even if the imaging modality referred to is not the most commonly used one. Thus, the one or more processors 106 take into account that a practitioner is in a best position to determine certain diagnostic or prognostic options and do not interfere with the practitioner's practice.

In some examples, the one or more processors 106 may further adapt by modifying the options or suggestions presented based on feedback from the device 108 regarding which diagnostic or prognostic mechanisms are selected in certain situations. For example, if CT is most commonly selected in the situation of back problems, the one or more processors 106 may adapt by presenting CT instead of MRI as the option 404 (a primary option) rather than as one of the alternative options 406.

The probabilities of relevance 414 and 416 may also be adjusted based on input received from the device 108. For example, if the input from the device 108 indicates that CT is much more frequently used compared to MRI, the probabilities of relevance of options or suggestions associated with or including CT may be adjusted to be higher. Although particular examples of diseases or medical conditions are mentioned for the sake of illustration, the implementation of FIG. 4 may apply to any disease or medical condition.

Figure 5A:
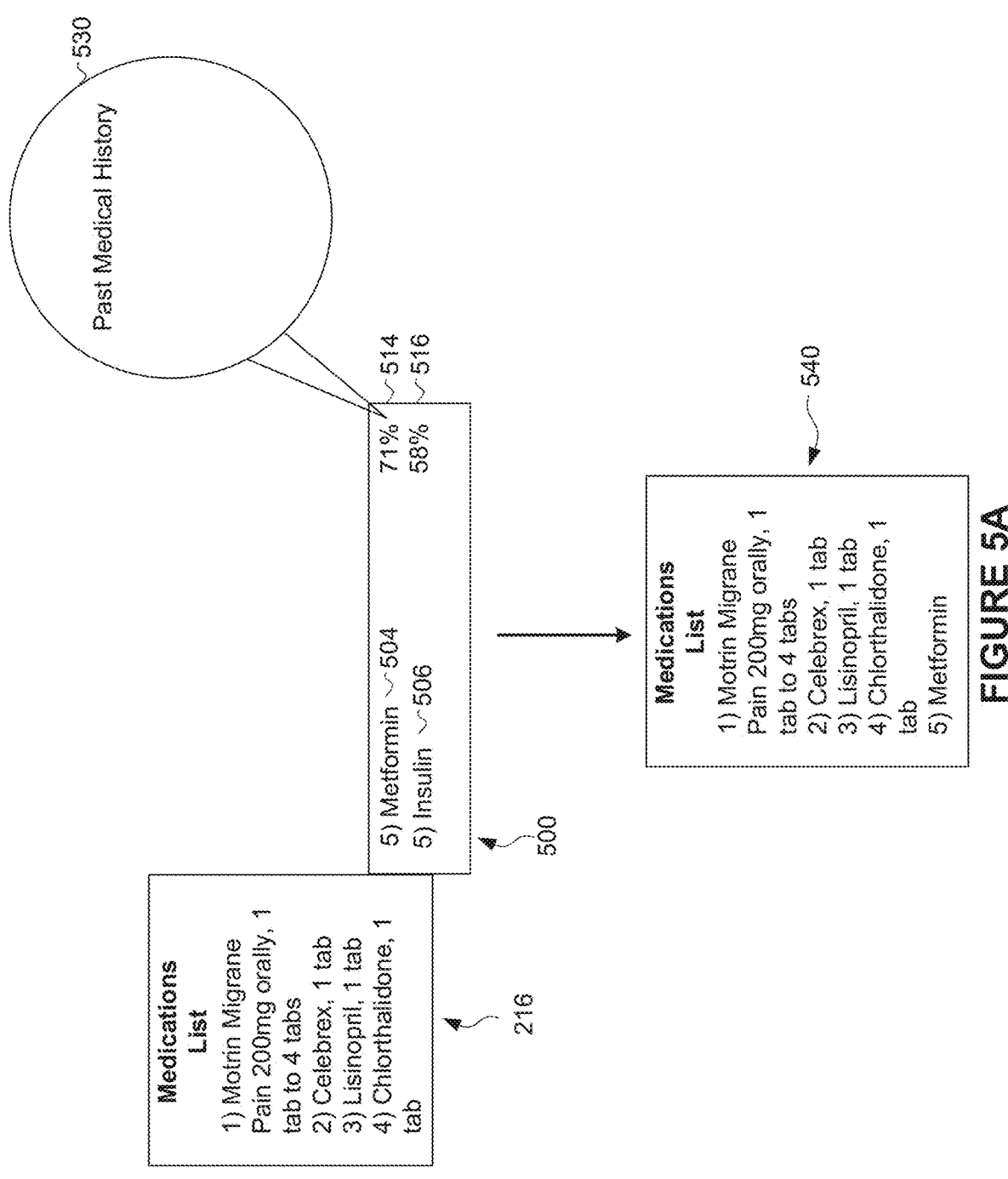

FIG. 5A illustrates an exemplary implementation of a mechanism of updating the digital health data platform by the one or more processors 106, showing how the records 104 of the patient 105 are updated following suggestions, or options, presented by the one or more processors 106. Relevant details provided with respect to other figures may also be applicable to the implementation shown in FIG. 5A. Sometimes, if the medications list window 216 does not include all medications that the patient 105 is currently being administered or prescribed, the one or more processors 106 may infer or determine other medications that the patient 105 may actually be administered or prescribed based on context presented from data in either or both of the panels 200 and 250 and/or from other data such as that included in the database 102 and pharmacy claims data.

For example, the one or more processors 106 may extract data from the past medical history window 210 that the patient 205 is diabetic, and associate a reference related to diabetes with a drug specifically tailored to diabetic patients. That is, if the one or more processors 106 fail to detect any reference to such a drug in the medications list window 216, the one or more processors 106 may determine or infer that the medications list window 216 is missing that drug. The one or more processors 106 may determine one or more particular drugs that are commonly used on diabetic patients, and/or commonly used on diabetic patients having same or similar demographic characteristics as the patient 105 and output these particular drugs as options or suggestions. Thus, the one or more processors 106 may output in a window 500 to the device 108, an option 504 which includes the drug metformin, and an alternative option 506 which includes the drug insulin, while indicating that probabilities of relevance 514 and 516 are 71% and 58%, respectively. The window 500 may be implemented either as an overlay over existing medical data or in a sidebar to a side of the existing medical data, which may be presented in the panel 200 or 250. The one or more processors 106 may further present a tooltip, pop-out menu, popup window, or a hover box 530 to provide a reasoning or justification as support for the option 504 and the alternative option 506. For example, the tooltip, pop-out menu, popup window, or the hover box 530 shows that the medications indicated in the option 504 and the alternative option 506 may be necessary based on data from the past medical history window 210. In FIG. 5A, the one or more processors 106 may detect that an input from the device 108 indicates a selection of metformin, and present an updated medications list window 540 that includes metformin.

The one or more processors 106 may be trained using a training dataset having inputs of certain problems, conditions or diseases, and outputs of what types of medications and/or particular medications associated with those problems, conditions or diseases. For example, the one or more processors 106 may recognize and/or associate types of medications that are used for diabetes, in order to determine whether the medications list window 216 is missing a medication. The one or more processors 106 may further be trained to determine which types of medications are frequently utilized to treat particular conditions or problems for particular demographics of patients. For example, the one or more processors 106 may be trained to recognize that metformin is most frequently used to treat diabetes patients of a particular demographic type same or similar to that of the patient 205 so that the one or more processors 106 will present metformin as the option 504. However, if the one or more processors 106 detect that a diabetes medication is referred to in the medications list window 216, the one or more processors 106 may refrain from presenting an option of another medication, even if that diabetes medication referred to is not metformin or is not commonly used. Thus, the one or more processors 106 take into account that a practitioner is in a best position to determine certain medications and do not interfere with the practitioner's practice.

In some examples, the one or more processors 106 may further adapt by modifying the options or suggestions presented based on feedback from the device 108 regarding which medications are selected in certain situations. For example, if metformin is most commonly selected to treat diabetic patients of a certain demographic and insulin is most commonly selected to treat diabetic patients of a different demographic, the one or more processors 106 may adapt by presenting the medications most commonly used as the option 504 depending on which demographic a patient fits in.

The probabilities of relevance 514 and 516 may also be adjusted based on input received from the device 108. For example, the higher a frequency at which a particular medication is selected to treat or address a given disease or medical condition and/or a patient demographic, the higher the probability of relevance of an option or suggestion associated with that particular medication. Although particular examples of diseases or medical conditions are mentioned for the sake of illustration, the implementation of FIG. 5A may apply to any disease or medical condition.

Figure 5B:
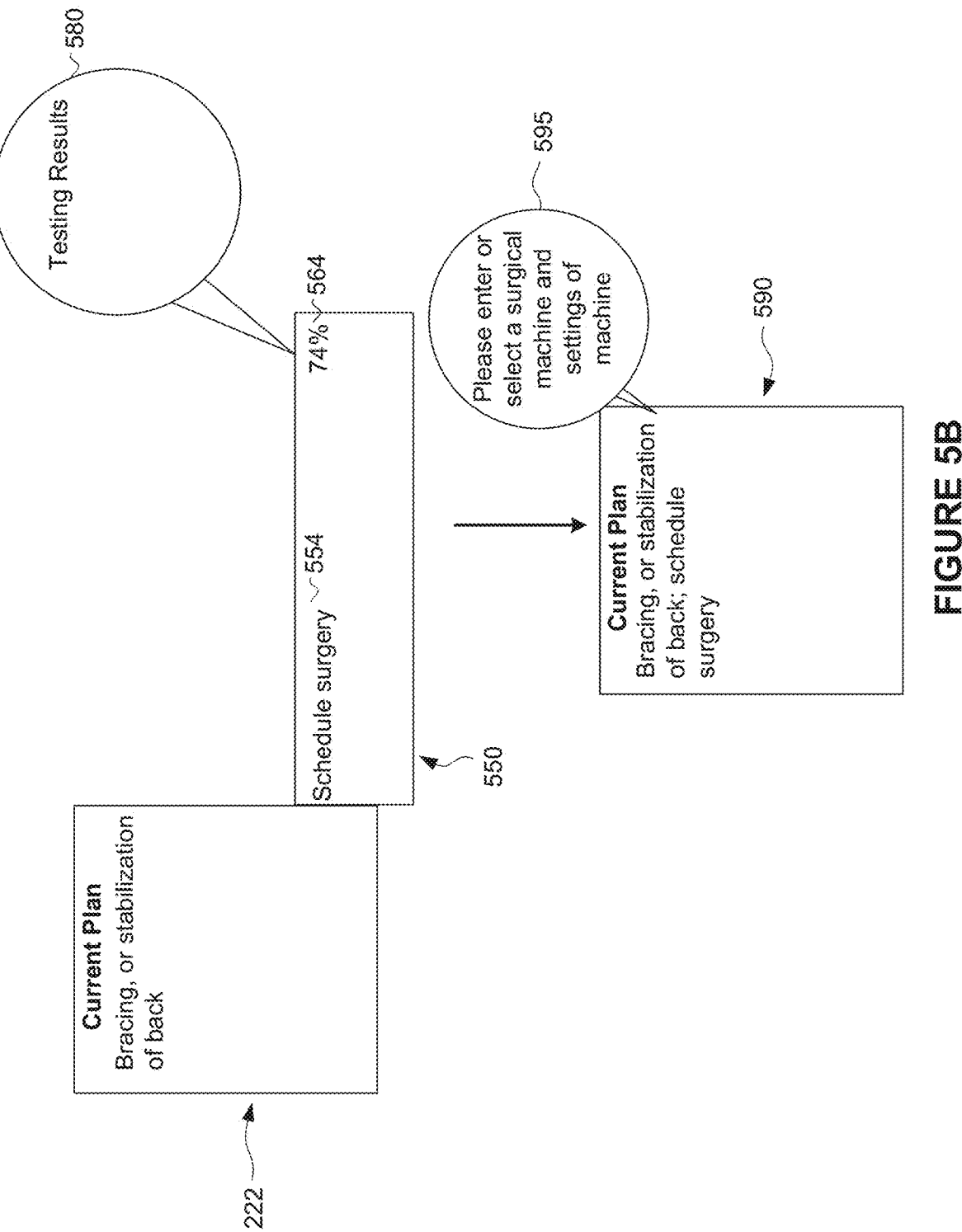

FIG. 5B illustrates an exemplary implementation of a mechanism of updating the digital health data platform by the one or more processors 106, showing how the records 104 of the patient 105 are updated following suggestions, or options, presented by the one or more processors 106. Relevant details provided with respect to other figures may also be applicable to the implementation shown in FIG. 5B. The one or more processors 106 may determine further options or suggestions to supplement a current entry in the current plan window 222. In some embodiments, the one or more processors 106 may determine, from other data presented in the panel 200 and/or the panel 250, that further treatment such as surgery may be required.

In some examples, the one or more processors 106 may analyze updated data in the testing results, such as the MRI data 254, to determine a presence of a particular medical condition such as a fracture. The process of determining a presence of a condition, such as a fracture, may involve semantic segmentation and/or instance segmentation to determine boundaries between different types of tissues such as bone, joints, muscle, and fat, and determine different boundaries between a same type of tissue. The one or more processors 106 may be trained using a training dataset that includes inputs of reference image data that shows boundaries among tissues of a normal patient and of a patient that exhibits a particular medical condition, and outputs indicating whether or not that reference image data is of a normal patient. For example, if a determined boundary in a current patient such as the patient 105 is not present in the reference image data of a normal patient, the one or more processors 106 may infer or determine that the determined boundary in the current patient corresponds to a fracture or other medical condition.

The performing of semantic and/or instance segmentation may be by the same machine learning model that was trained based on text inputs. In particular, the same machine learning model that was trained to detect ambiguous or erroneous entries using input training data may also be trained, or otherwise configured, to perform semantic segmentation and/or instance segmentation. In some embodiments, the machine learning model may include an ensemble machine learning model that is trained to perform both segmentation and detection of ambiguous or erroneous text entries.

If the one or more processors 106 determine the presence of a fracture or other medical condition, the one or more processors 106 may determine that further treatment beyond that provided in the current plan window 222 should be suggested. For example, the one or more processors 106 may associate a fracture with a surgical procedure. Thus, the one or more processors 106 may determine if any reference to a surgery or particular surgical procedure is included in either the panel 200 or the panel 250. If the one or more processors 106 determine that no such reference is included, the one or more processors 106 may present or suggest, in a window 550, that an option 554 of scheduling a surgery be added to the current plan window 222. The window 550 may be implemented either as an overlay over existing medical data or in a sidebar to a side of the existing medical data, which may be presented in the panel 200 or 250. A probability of relevance 564 of 74% may be presented in the window 550 and be indicative of a relative frequency of a fracture in that region of a body requiring a surgical procedure for a particular demographic. The one or more processors 106 may further present a tooltip, pop-out menu, popup window, or a hover box 580 to provide a reasoning or justification as support for the option 554. For example, the tooltip, pop-out menu, popup window, or the hover box 580 shows that the measures indicated in the option 554 may be necessary based on data from the testing results in the panel 250. In FIG. 5B, the one or more processors 106 may detect that an input from the device 108 indicates that the option 554 has been accepted. The one or more processors 106 may present an updated current plan window 590 that includes scheduling surgery.

Subsequently, the one or more processors 106 may present, to the device 108, a prompt to select a machine to conduct a surgery and protocol and/or settings of implementing a surgical procedure on the selected machine. For example, the prompt may be in a form of a dialog 595. In some examples, the dialog 595 may be a pop-up window which enables a selection from predetermined settings or a manual entry from the device 108 of the protocol and/or settings to be followed. In some examples, the predetermined settings may include commonly used settings, such as settings commonly used in a particular type of surgical procedure. In some examples, the dialog 595 may provide an option on the device 108 to select a commonly used setting while modifying specific parameters or properties of that setting. The one or more processors 106 may then communicate with the selected surgical machine (e.g., the surgical machine 114) and transmit the settings and/or protocol to be applied, to initialize the surgical machine 114.

The one or more processors 106 may be trained using training data having inputs of particular medical conditions and outputs of what measures, such as surgery or particular types of surgery, are implemented when those particular medical conditions occur. For example, the one or more processors 106 may be trained to recognize that surgery is commonly used in situations of fractures. In some examples, the one or more processors 106 may be trained to associate a fracture, as indicated or detected from somewhere in the panel 200 or 250, with a surgery. If the one or more processors 106 do not detect that any reference to a surgery or particular type of surgery is present in the panel 200 or 250, then the one or more processors 106 may determine that an option of a surgery should be, or is to be, presented at the device 108. However, if the one or more processors 106 do detect that a surgery or particular type of surgery is referred to on the applicable date somewhere in the panel 200 or 250, the one or more processors 106 may refrain from presenting an option of a surgery, even if that surgery referred to is not a most commonly used type of surgery in that scenario. In such a manner, the one or more processors 106 take into account that a practitioner is in a best position to determine certain surgical options and do not interfere with the practitioner's practice.

In some examples, the one or more processors 106 may further adapt by modifying the options or suggestions presented based on feedback from the device 108 regarding which surgical procedures are selected in certain situations. For example, if lumbar fusion is most commonly selected in the situation of a spinal or back fracture, the one or more processors 106 may adapt by presenting lumbar fusion as the option 554 in relevant scenarios. The probability of relevance 564 may also be adjusted based on input received from the device 108. For example, if the input from the device 108 indicates that lumbar fusion is most commonly used in spinal fractures, the probabilities of relevance of options or suggestions associated with or including lumbar fusion associated with spinal fractures may be adjusted to be higher. Although particular examples of diseases or medical conditions are mentioned for the sake of illustration, the implementation of FIG. 5B may apply to any disease or medical condition.

Figure 6:
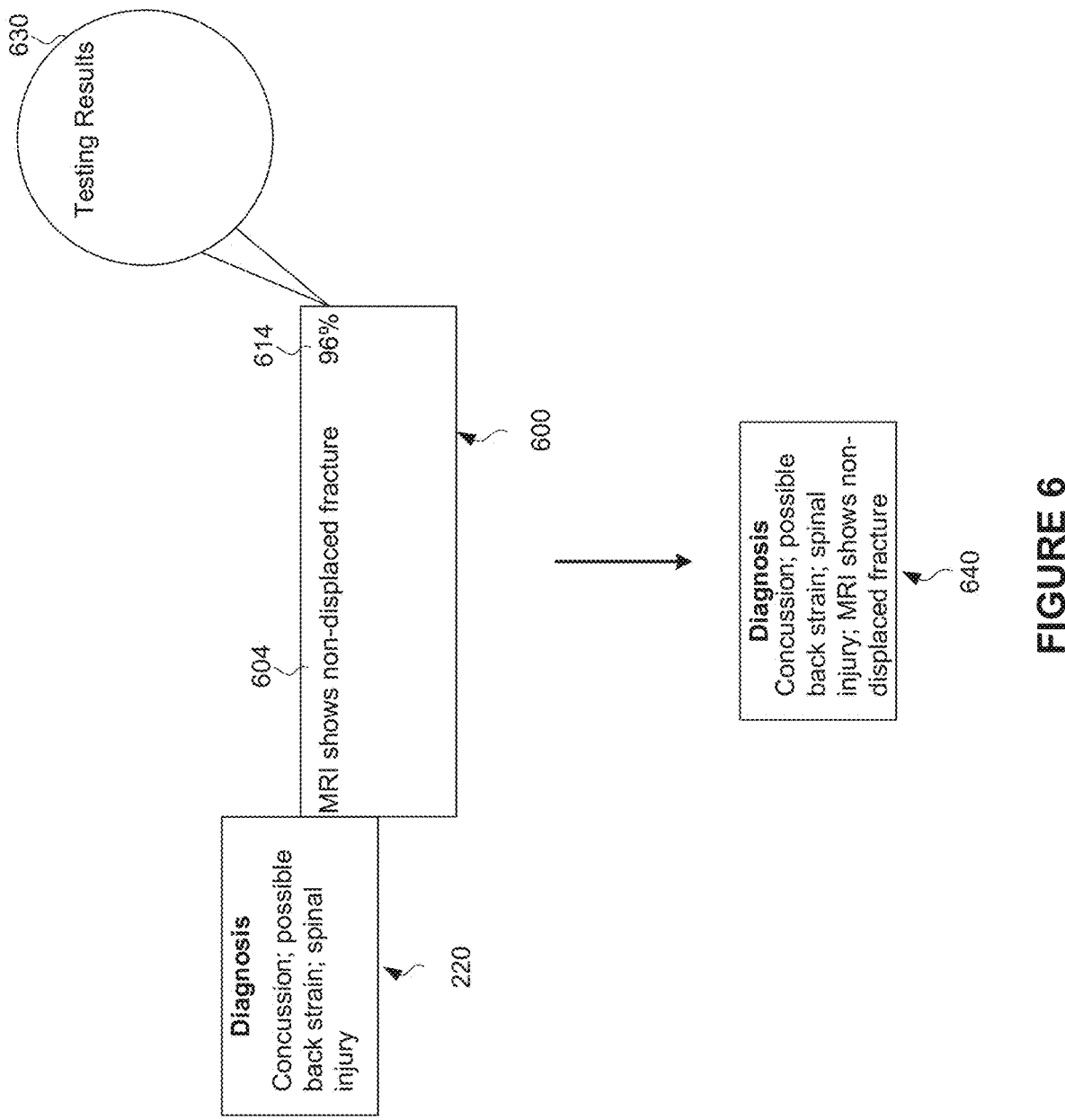

FIG. 6 illustrates an exemplary implementation of a mechanism of updating the digital health data platform by the one or more processors 106, showing how the records 104 of the patient 105 are updated following suggestions, or options, presented by the one or more processors 106. Relevant details provided with respect to other figures may also be applicable to the implementation shown in FIG. 6. The one or more processors 106 may determine further options or suggestions to supplement a current entry in the diagnosis window 220 based on updated testing data. In some embodiments, once the one or more processors 106 detect that testing data, for example, shown in the MRI data 254, shows a non-displaced fracture, the one or more processors 106 may present, to the device 108, an option or suggestion 604, in a window 600, to incorporate this information. A probability of relevance 614 of 96% may also be presented in the window 600 and indicative of a degree of certainty that the MRI data 254 and/or other data does indicate such a fracture. The window 600 may be implemented either as an overlay over existing medical data or in a sidebar to a side of the existing medical data, which may be presented in the panel 200 or 250. In FIG. 6, the one or more processors 106 may detect that an input from the device 108 indicates that the option 604 has been accepted. The one or more processors 106 may present an updated diagnosis window 640 that includes information of the MRI data.

In some examples, the one or more processors 106 may further adapt by modifying the options or suggestions presented based on feedback from the device 108. For example, if the device 108 overrides the option 604 and instead provides manually entered text, "MRI shows fracture," which may suggest that more succinct and general language is preferred, the one or more processors 106 may adjust by providing more succinct and general options or suggestions in the future. Although particular examples of diseases or medical conditions are mentioned for the sake of illustration, the implementation of FIG. 6 may apply to any disease or medical condition.

Figure 7:
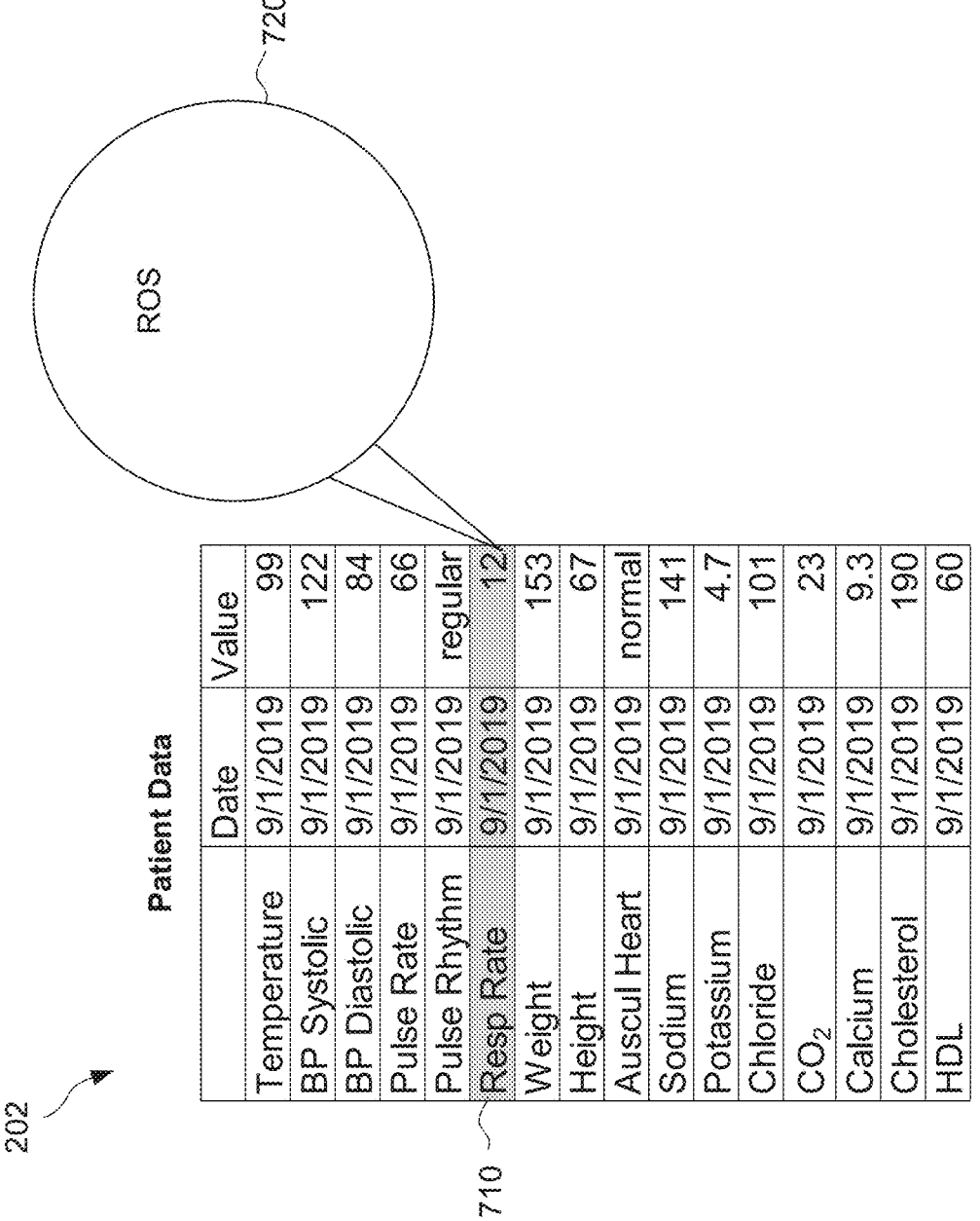

FIG. 7 illustrates an exemplary implementation of a mechanism of updating the digital health data platform by the one or more processors 106, showing how potentially erroneous entries are detected. Relevant details provided with respect to other figures may also be applicable to the implementation shown in FIG. 7. As an example, some entries in the patient chart 202, such as respiratory rate, may be commonly filled in without actual measurement by a practitioner. In other words, the practitioner may simply fill in "12," "14," or "16" in an effort to save time, or fill in a rough estimate without a precise measurement. Thus, the one or more processors 106 may recognize which entries are commonly filled in without actual measurement, and flag or otherwise indicate such entries. In some examples, the one or more processors 106 may flag such entries, or any entries in the patient chart 202 or elsewhere in the panel 200, if they appear to be inconsistent with other entries in the panel 200. In FIG. 7, the one or more processors 106 may flag an entry 710 indicating that a respiratory rate was 12 beats per minute because information in the ROS window 208 indicates that the patient 105 had rapid breathing, which appears to be inconsistent. The one or more processors 106 may further indicate, in a tooltip, pop-out menu, popup window, or a hover box 720, that the ROS window 208 includes potentially conflicting or contradictory data. The one or more processors 106, upon detecting potentially conflicting or contradictory data, may flag an entry that is more or most likely to be erroneous. Here, the one or more processors 106 may determine that the entry 710 in the patient chart 202 is more likely to be erroneous compared to the entry in the ROS window 208, in part because the respiratory rate is commonly filled out without measuring and the entry in the ROS window 208 requires a manual input by a practitioner.

In some embodiments, the one or more processors 106 may detect whether an entry is actually linked to or verified by a recorded sensor measurement. For example, the one or more processors 106 may determine whether a source, such as a sensor, exists to verify each entry in the patient chart 202, in other words, whether each entry can be traced to or is verified by a recorded sensor measurement. In such examples, a measurement from a sensor may be recorded and automatically populated into the patient chart 202. If the one or more processors 106 determine that an entry is not verified by a sensor measurement, the one or more processors 106 may flag that entry and/or more stringently verify, compared to other entries, whether that entry is consistent with other data, for example, in the panel 200.

The one or more processors 106 may be trained using training data having inputs of conflicting or contradictory data and outputs indicating particular data entries are erroneous and which data entries are correct. The one or more processors 106 may be trained to recognize particular factors or criteria that increase a likelihood of an entry being erroneous, such as, case of inputting the entry, whether the entry matches a commonly inputted round number such as "12," "14," or "16," and/or whether the parameter being measured in the entry is one that would otherwise be time-intensive to actually measure or is known as a parameter that is commonly inputted without an actual measurement. Although particular examples of diseases or medical conditions are mentioned for the sake of illustration, the implementation of FIG. 7 may apply to any disease or medical condition.

In some embodiments, the one or more processors 106 may be configured to identifying an entry, for example, in the patient chart 202 in which a numeral is missing a subsequent unit of measurement and which may be confusing. The one or more processors 106 may determine a particular unit of measurement to append to an end of the numeral based on the context of the entry and other data in the panels 200 and 250. The one or more processors 106 may flag the numeral that is missing a subsequent unit of measurement. However, certain numerals do not require a subsequent unit of measurement because they may be widely understood. In such scenarios, the one or more processors 106 may not flag such a numeral.

Figure 8:
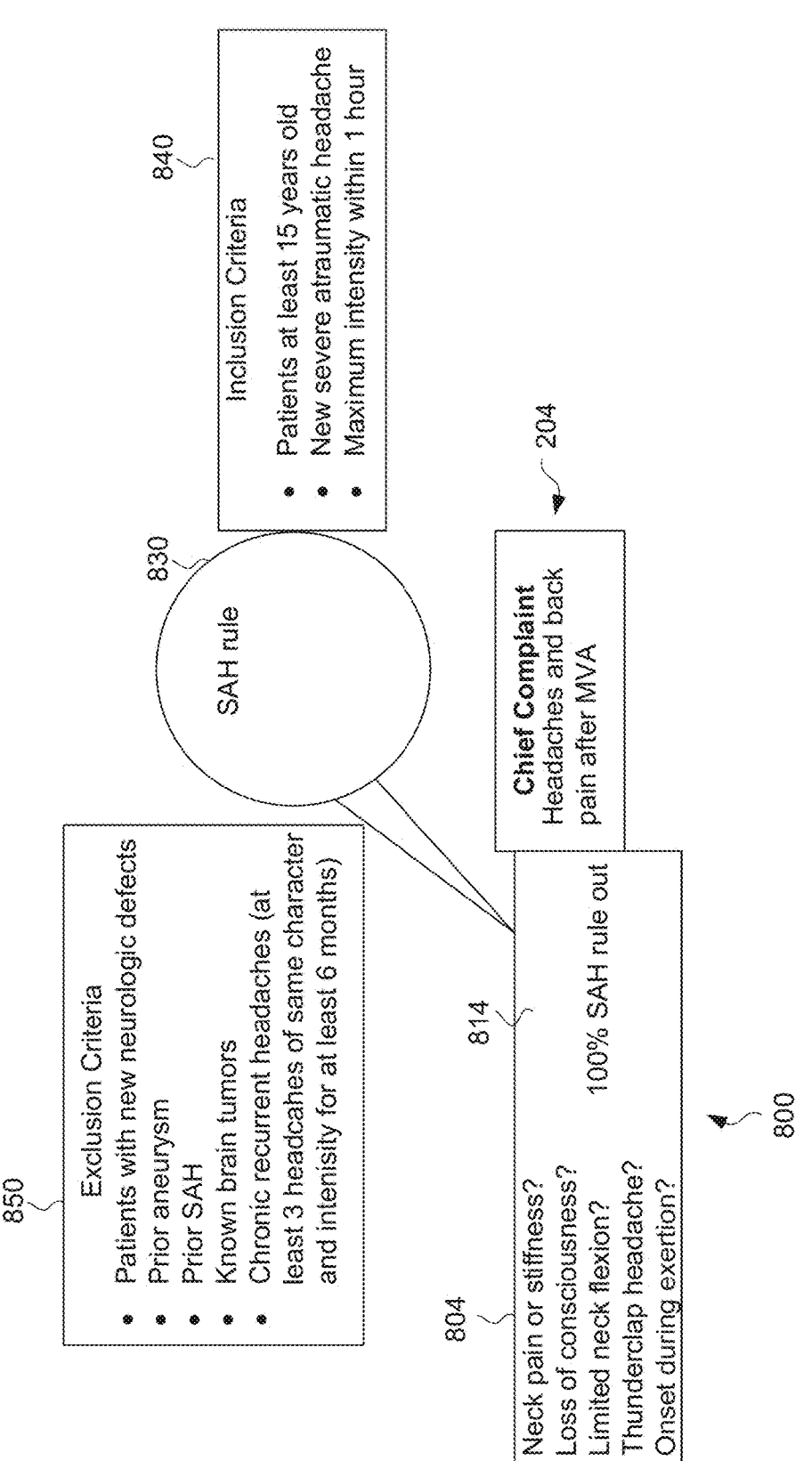

FIG. 8 illustrates an exemplary implementation of a mechanism of updating the digital health data platform by the one or more processors 106, showing a mechanism by which additional information about the patient 105 may be requested in order to determine or rule out an existence of additional conditions. Relevant details provided with respect to other figures may also be applicable to the implementation shown in FIG. 8.

As an example, the one or more processors 106 may determine that symptoms listed in the chief complaints window 204 include headaches. The one or more processors 106 may recognize that headaches may indicate other conditions such as subarachnoid hemorrhage (SAH) based on diagnostic tests, methods, or protocols programmed into the one or more processors 106. For example, the one or more processors 106 may present, to the device 108, a window 800 that includes additional questions 804 to provide further clarity to determine or rule out an existence of additional conditions. In the window 800, the one or more processors 106 may further indicate a particular condition 814 that could be confirmed or ruled out by the additional questions 804. In some examples, if the particular condition 814 cannot be confirmed or ruled out with certainty, the window 800 also indicates a likelihood that the particular condition can be confirmed or ruled out. The window 800 may be implemented either as an overlay over existing medical data or in a sidebar to a side of the existing medical data, which may be presented in the panel 200 or 250.

The one or more processors 106 may further present a tooltip, pop-out menu, popup window, or a hover box 830 to indicate a particular diagnostic test, method, or protocol used to determine whether the particular condition 814 can be confirmed or ruled out. Furthermore, the one or more processors 106 may present, as additional tooltips, pop-out menus, popup windows, or hover boxes 840 and 850, inclusion criteria and exclusion criteria of the diagnostic test, respectively. Moreover, the one or more processors 106 may present perils and pitfalls of the particular diagnostic test, method, or protocol, manners or situations in which the particular diagnostic test, method, or protocol may best be used. In some examples, the one or more processors 106 may further be programmed to execute prognostic methods, algorithms, and/or determinations of treatment options. In some examples, the one or more processors 106 may suggest which of possible prognostic methods, algorithms, and/or determinations of treatment options are most applicable to a current condition being treated. The suggestions may be presented at a sidebar to a side of the existing medical data, which may be presented in the panel 200 or 250. For each of the suggestions, the one or more processors 106 may present guidelines, whether that suggestion is still applicable or relevant in view of other diagnostic methods or tests, whether that suggestion has already been implemented, for example, if a diagnostic method has already been performed on that patient. Such an implementation takes into account that the diagnostic tests, methods, or protocols are not black and white but are blunt tools generally based on population studies and that the practitioner is in a best position to determine whether to use and a manner in which to use a particular diagnostic test, method, or protocol, and execute prognostic methods, algorithms, and/or determinations of treatment options.

Once the one or more processors 106 receives an input from the device 108, the one or more processors 106 may carry out the diagnostic test, method, or protocol and output or populate results of the diagnostic test, method, or protocol to one or more appropriate windows of the panel 200 and/or the panel 250. In some examples, a frequency or a time of populating the results to an appropriate window in one or both of the panels 200 and/or 250 may be predetermined or manually determined. In some examples, the results including a most recent result and all results in a recent timeframe, such as in the previous 24 or 72 hours, may be populated, along with native macros or dot phrases, into an appropriate window in one or both of the panels 200 and/or 250 such as, for example, the patient chart 202. Although particular examples of diseases or medical conditions are mentioned for the sake of illustration, the implementation of FIG. 8 may apply to any disease or medical condition.

FIGS. 9-15, 16A-16C, 17-20, 21A-21C, and 22 illustrate exemplary implementations of diagnostic tests, methods, or protocols, prognostic methods, algorithms, and/or determinations of treatment options, which may be implemented in conjunction with any of the implementations of the previous FIGS. 1-8. For example, the exemplary implementations shown in FIGS. 9-15, 16A-16C, and 17-19, along with other implementations including additional diagnostic tests, methods, or protocols, prognostic methods, algorithms, and/or determinations of treatment options, may be programmed into the one or more processors 106. The programs may provide specific data with which to update the digital health data platform and to determine further diagnostic or prognostic measures or treatments. For example, at least a portion of any outputs, determinations, and/or computations from any of the diagnostic tests, methods, or protocols, prognostic methods, algorithms, and/or determinations of treatment options, such as those illustrated in FIGS. 9-15, 16A-16C, 17-20, 21A-21C, and 22, may be provided as options or suggestions by the one or more processors 106.

Figures 9, 10:
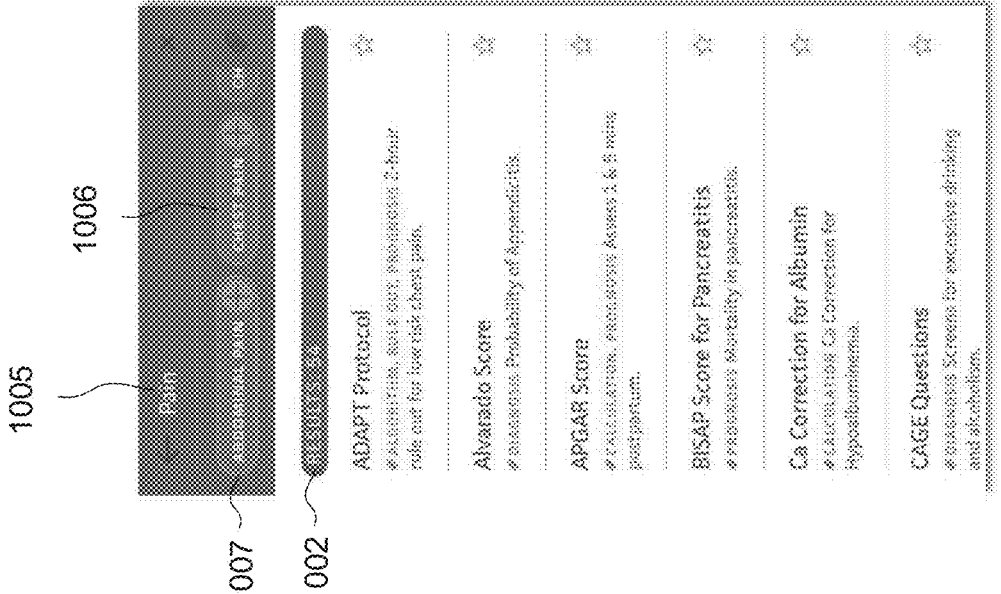

FIG. 9 illustrates a graphical interface 900 of a diagnostic test, method, or protocol. The graphical interface 900 may be presented on a screen of the device 108, either as an overlay over existing medical data or in a sidebar to a side of the existing medical data, which may be presented in the panel 200 or 250. The graphical interface 900 may include a main menu 903 and a partial listing of available diagnostic tests, methods, or protocols, prognostic methods, algorithms, and/or treatment options in panel 902.

FIG. 10 illustrates a search interface which includes a top search box 1005, a filter/tag region 1007, and a main panel 1002 for displaying the search results. In the example of FIG. 10, if "Pain" is entered as a search query, the system conducts one or more searches in one or more databases.

The term "database" refers generically to any collection of information that is structured, either as a traditional relation table or otherwise, to enable searches and updates. A database can be located locally on a computer device from which the one or more processors 106 receive a search query and conduct a search, or remotely through a computer network. In one embodiment of the present technology, the computing device that includes the electronic screen that displays the graphical interface 900 stores a local copy (or partial copy) of the database(s) in which the searches are conducted. The local copy enables use of the system when no internet is accessible, for instance, at an underground emergency room.

The local copy can be updated on demand or when a predetermined set of criteria are met (e.g., update frequency or schedule). In some embodiments, the program code in the system for carrying out the search and implementation of diagnostic tests, methods, or protocols, prognostic methods, algorithms, and/or determinations of treatment options can also be updated when a new version is available or when the program code changes. In one embodiment, updates to the program code and to the local copy of the database are independent of each other. That is, the system checks whether the content of the database needs updating (e.g., by comparing version number, content size, or the content itself) independently from checking whether the program code (e.g., the software package or smart phone app) needs updating. In some embodiments, each of the diagnostic tests, methods, or protocols, prognostic methods, algorithms, and/ or determinations of treatment options can be independently checked and updated. For instance, each diagnostic test, method, or protocol, prognostic method, algorithm, and/or determination of a treatment option is associated with a version tag (e.g., MD5/ETag) which changes when the diagnostic test, method, or protocol, prognostic method, algorithm, and/or determination of a treatment option is updated. Thus, when the version tag for the diagnostic test, method, or protocol, prognostic method, algorithm, and/or determination of a treatment option is different between the local copy and the server, an update is appropriate and can be triggered.

One of the searches entails looking up the search query (e.g., "Pain") against each diagnostic test, method, or protocol, prognostic method, algorithm, and/or determination of a treatment option, in the database. To this end, each entry associated with the diagnostic test, method, or protocol, prognostic method, algorithm, and/or determination of a treatment option in the database is associated with suitable annotations and categorizations, as further explained below.

As used herein, a diagnostic test, method, or protocol, prognostic method, algorithm, and/or determination of a treatment option may include a computational tool (or corresponding formula, equation or clinical decision rule) that produces a result useful in a medical setting, such as diagnosis, prognosis, health care evaluation, and treatment optimization, without limitation. The computational tool can take inputs of different types, such as numerical inputs, discrete inputs, categorical input (e.g., yes/no) or does not require an input (e.g., indication of staging of cancers).

A diagnostic test, method, or protocol, prognostic method, algorithm, and/or determination of a treatment option can be annotated with definitions or description for each of its inputs, the output, the purpose, the interpretation of the likely output, references relating to the diagnostic test, method, or protocol, prognostic method, algorithm, and/or determination of a treatment option, and originator of the diagnostic test, method, or protocol, prognostic method, algorithm, and/or determination of a treatment option. Each diagnostic test, method, or protocol, prognostic method, algorithm, and/or determination of a treatment option can also be associated with a plurality of keywords (e.g., symptoms, complaints) that are likely used for searching for the diagnostic test, method, or protocol, prognostic method, algorithm, and/or determination of a treatment option. Moreover, the keyword list can further include synonym, acronyms and abbreviations. Each of these types of information can be used for matching the diagnostic test, method, or protocol, prognostic method, algorithm, and/or determination of a treatment option with a search query.

A diagnostic test, method, or protocol, prognostic method, algorithm, and/or determination of a treatment option can be associated with one or more "tags" useful for the search. Tags are generated on different types of categorizations, such as the following:

1. Specialty (e.g. cardiology, emergency medicine)
2. Organ system (e.g. cardiovascular; renal, pulmonary)

3. Disease (e.g. heart attack, pulmonary embolism, pneumonia)
4. Chief complaint (e.g. chest pain, shortness of breath, headache)
5. Function (e.g. rule-out, diagnose, prognosticate, treat)

In one embodiment, at least a diagnostic test, method, or protocol, prognostic method, algorithm, and/or determination of a treatment option is annotated with at least one of the above categories of tags, i.e., one of specialty, organ system, disease, chief complaint, or function. In one embodiment, at least a diagnostic test, method, or protocol, prognostic method, algorithm, and/or determination of a treatment option is annotated at least with two of the above categories of tags. In some aspects, the two categories include at least function. In some aspects, the two categories include at least disease or chief complaint. In some aspects, at least a diagnostic test, method, or protocol, prognostic method, algorithm, and/or determination of a treatment option is annotated at least with three of the above categories of tags. In some aspects, the three categories include at least a function. In some aspects, the three categories include at least disease or chief complaint. In some aspects, the three categories include at least disease, chief complaint and function.

Conversely, each tag is associated with one or more diagnostic tests, methods, or protocols, prognostic methods, algorithms, and/or determinations of treatment options. Moreover, each tag can be further annotated with keywords or synonym, acronyms and abbreviations of the keywords. One way of generating such a keyword list is to incorporate the keywords from each diagnostic test, method, or protocol, prognostic method, algorithm, and/or determination of a treatment option associated with the tag.

To further facilitate search, the system can be configured to further display one or more suggested filters based on the search query, which can include the tags as well as other information. In one embodiment, when a search query is entered, the system searches through all tags and identify those that are associated with the search query (e.g., as associated keywords). The identified tags are then provided to the device 108, which may provide an input to narrow down the search results.

The filters do not have to be tags, however. In one embodiment, a filter is any category of one or more diagnostic tests, methods, or protocols, prognostic methods, algorithms, and/or determinations of treatment options. In another embodiment, the filter is a word, phrase or abbreviation that relates to a search query. The relationship can be pre-determined, such as a tag that is associated with a list of keywords. In this example, when one of the keywords is used as the search query, the tag is identified as a filter for potential use.

As illustrated in FIG. 10, when the search term "Pain" is entered, the system also searches through all filters and has identified, for instance, "Abdominal Pain" and "Chest Pain" as potential filters 1006. The one or more processors 106 may detect a selection of a particular filter, for example, from the device 108, which may occur when a user clicks on the particular filter. The selected particular filter may then be left at the filter list (the other, unused filters are then cleared), as shown in FIG. 11. Here, when the filter "Chest Pain" is applied, the search results are accordingly narrowed down.

In some embodiments, a filter can be identified dynamically on the fly. For instance, when the search query is searched through the database, related diagnostic tests, methods, or protocols, prognostic methods, algorithms, and/ or determinations of treatment options, tags and/or predetermined filters can be identified. Data mining can then be applied on these initial search results to identify major themes (e.g., clusters) among the search results. For instance, words and categories that appear most frequently can be automatically collected to be presented to the user as potential filters. For example, when the search query "Pain" is used, the words "chest", "headache", "NSAID", "bleeding", and "diagnosis" may be found to be the most frequently associated with the search results and thus are selected as filters.

Figure 13:
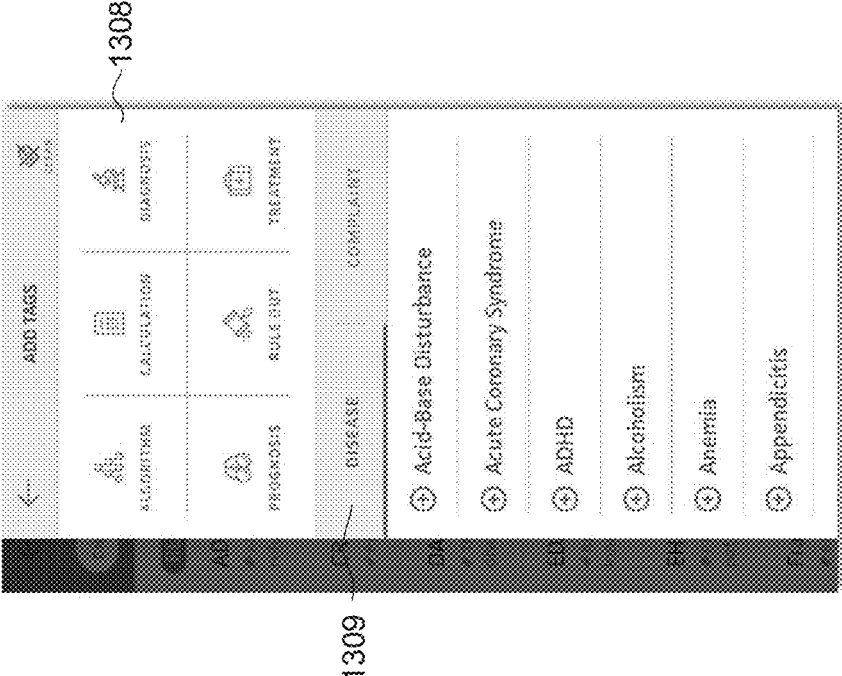

As apparent from FIGS. 12 and 13, each search result (i.e., a diagnostic test, method, or protocol, prognostic method, algorithm, and/or determination of a treatment option) shows up with a name, a brief description, and optionally one or more tags. The appearance of the tags here helps a user get familiar with the search system, and also provides a quick way to use the tags to filter results. For instance, on FIG. 11, the user sees that the algorithm "Framingham Risk Score," as well as other diagnostic tests, methods, or protocols, prognostic methods, algorithms, and/ or determinations of treatment options, are tagged as "Prognosis." By selecting the tag "Prognosis", all the search results are filtered with this tag (i.e., only diagnostic tests, methods, or protocols, prognostic methods, algorithms, and/ or determinations of treatment options having the tag "Prognosis" will remain in the search results).

Figures 14, 15:
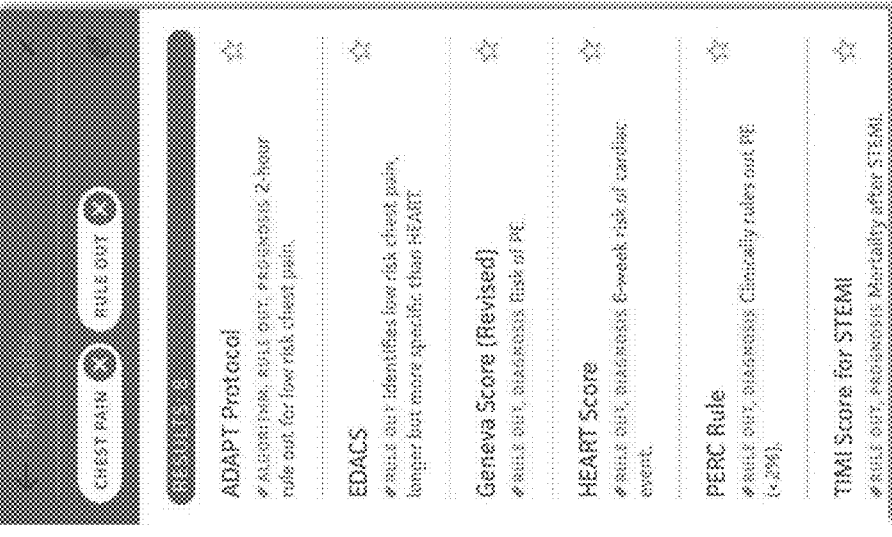

Another way of selecting and using tags is through the tag interface as illustrated in FIGS. 12 and 13. In FIG. 12, the interface includes a function tag panel 1208, a disease tag panel 1209, and a complaint panel 1210 with a listing of available complaint tags 1211. Here, because the filter/tag "Chest Pain" is already selected, it is greyed out. On the device 108, other function tags on the function tag panel 1208 may be selected. For example, "Diagnosis" may be selected. Accordingly, as shown in FIG. 14, only diagnostic tests, methods, or protocols, prognostic methods, algorithms, and/or determinations of treatment options with the "Diagnosis" tag, along with the already selected filter/tag "Chest Pain" are shown in the result panel. It is readily appreciated that more than one tag or filter can be used for each search. For instance, then the tag "Rule Out" is selected on top of "Chest Pain", the results are different as shown in FIG. 15.

In another example (not shown in figures), a doctor may want to know the chance a patient has a pulmonary embolism (PE) in order to determine the best way to work the patient up, so the doctor can search "Pulmonary Embolism" (a disease) and "Diagnose" (a function). In a related example, the patient will be diagnosed with a PE, and then the treating physician will choose "Pulmonary Embolism" and "Prognosticate" to find prognostic methods that help determine chance of mortality (for example, to help guide inpatient vs. outpatient treatment), and/or "Pulmonary Embolism" and "Treatment" to help choose which medicine and/or procedure are useful.

Figure 16B:
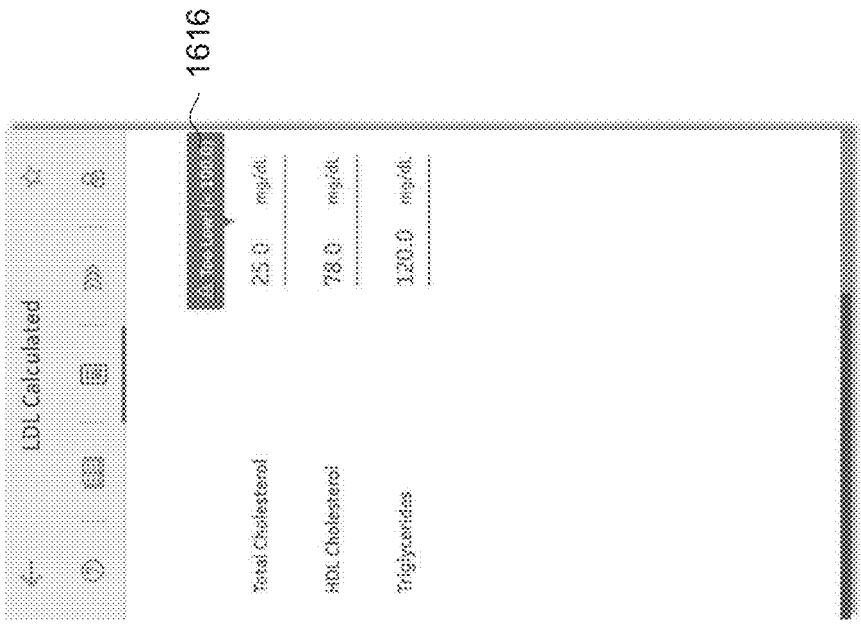
Figure 16A:
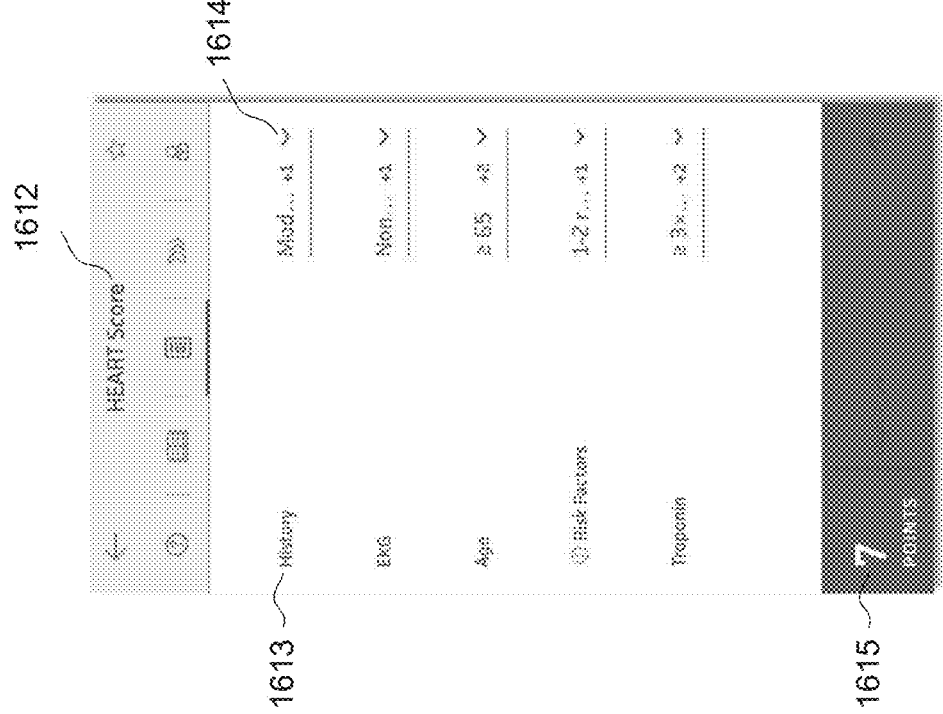
Figure 16C:
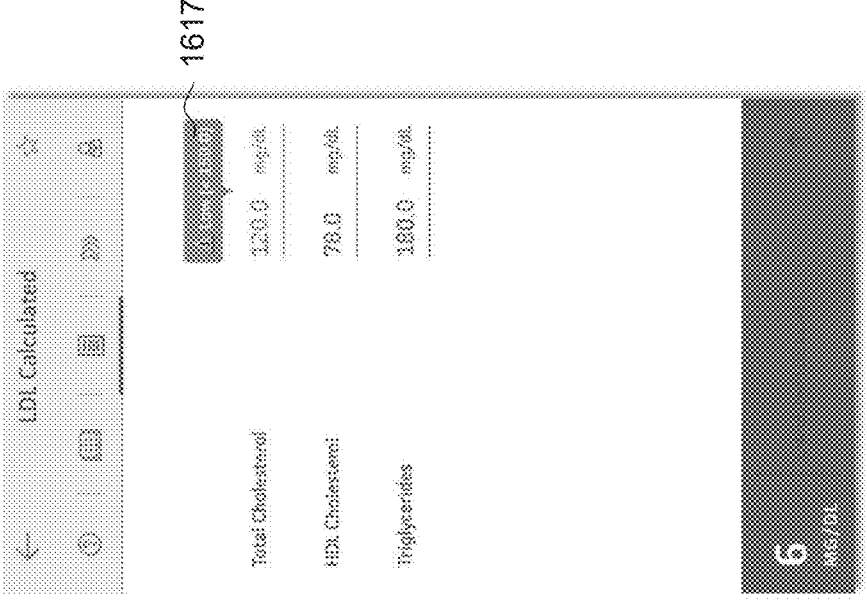
Figure 17:
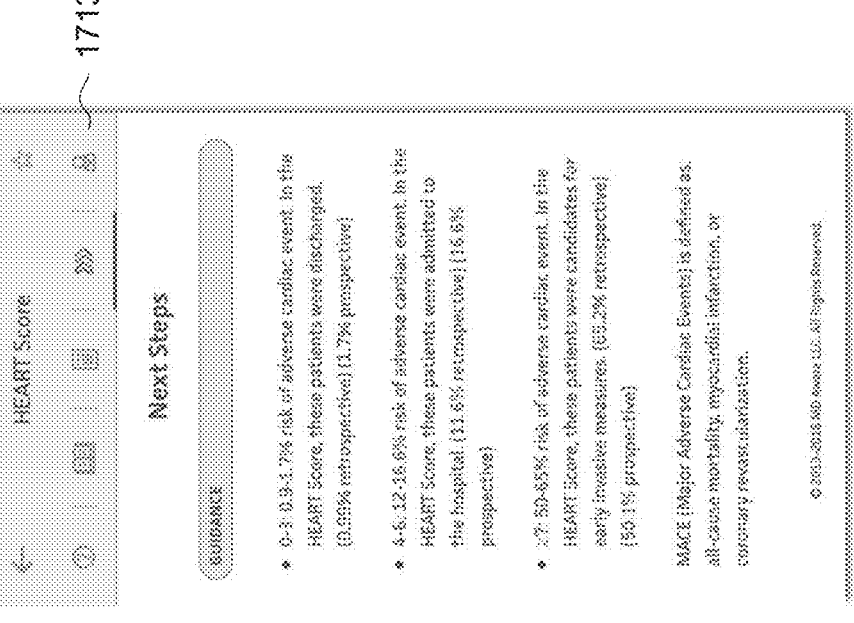
Figures 18, 19:
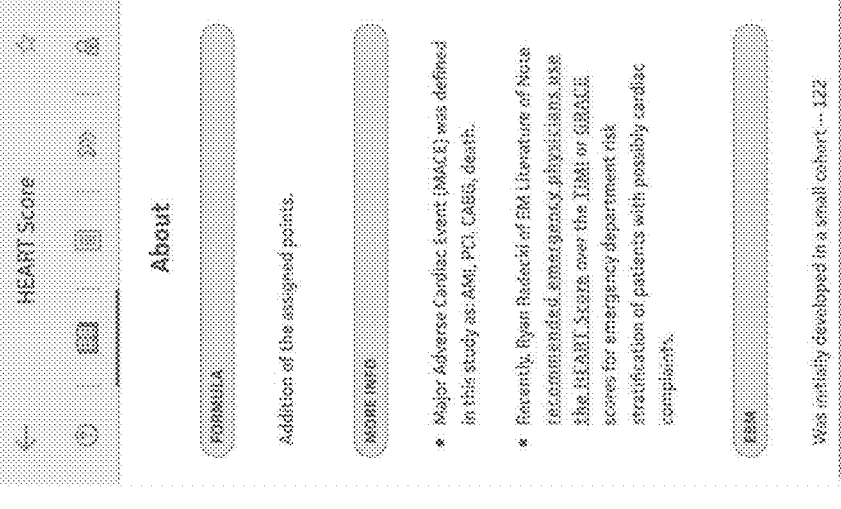

Once a diagnostic test, method, or protocol, prognostic method, algorithm, and/or determination of a treatment option is selected, the system presents a user interface onto the device 108 for using the diagnostic test, method, or protocol, prognostic method, algorithm, and/or determination of a treatment option, as illustrated in FIGS. 16A-16C. In FIG. 16A, a diagnostic test, method, or protocol, prognostic method, algorithm, and/or determination of a treatment option named "HEART Score" is shown at the top 1612, which takes a number of inputs 1614 for parameters 1613 including History, EKG, Age, Risk Factors, and Troponin. The format of the input depends on the type of data.

Once all requisite inputs are provided by the user, a result is shown at the bottom panel 1615.

In some scenarios, when a user enters an input that is beyond the acceptable or normal range, the system provides a mechanism for detecting such abnormality and providing an alert or even prompting the user to change the input. For instance, as illustrated in FIG. 16B, the system includes an acceptable range for a total cholesterol level of 100-500 mg/dL (which is optionally displayed when the user provides the input), and a normal range of 150-200 mg/dL (which is optionally displayed when the user provides the input). When the user enters 25, the system displays an alert 1616 indicating that the input is "Too Low! (<100.0)" in FIG. 16B.

Similarly, when the user enters 120, the system displays an alert 1617 indicating that the input may be outside an acceptable range, but is still a possible input in FIG. 16C. Nevertheless, a determination is performed and the result is displayed at the bottom.

In some embodiments, when a user, through the device 108, for example, clicks on the result shown on the display (e.g., at the bottom of the screen), the system brings up an interface showing more details of the results. Such further details include, for example, indication whether the result is normal or abnormal, the reference range, buttons or links to interpretation of the result, and/or intermediate results of the final result.

In some embodiments, when a user attempts to enter an input, at the input interface, the system display one or more of the following: default value, normal range of values, and acceptable range of values. In some embodiments, rather than providing a blank space for the user to enter a value, the system includes a default value and allows the user to change or update.

In some embodiments, to further assist the user, information relevant to the use, interpretation, and/or scientific resource can also be provided. For instance, by clicking on different tabs on the top, the user can view the "How to Use" (FIG. 18), "Next Steps" (FIG. 17), and "About" (FIG. 19) pages.

In some embodiments, a diagnostic test, method, or protocol, prognostic method, algorithm, and/or determination of a treatment option may be specific for COVID-19. FIG. 20 illustrates an implementation of a mechanism to diagnose and treat COVID-19 on a patient potentially or actually infected with COVID-19. In FIG. 20, the mechanism includes determining, subjectively, whether a patient has breathing or speech difficulties, determining a respiratory rate, a $PaO_2$ and $SpO_2$ level, and an analysis of a chest X-ray. These determination factors may be combined to assess a severity of COVID-19 and determine an appropriate treatment method. Other COVID-19 diagnosis, prognosis, and/or treatment options may be contemplated.

Figure 21A:
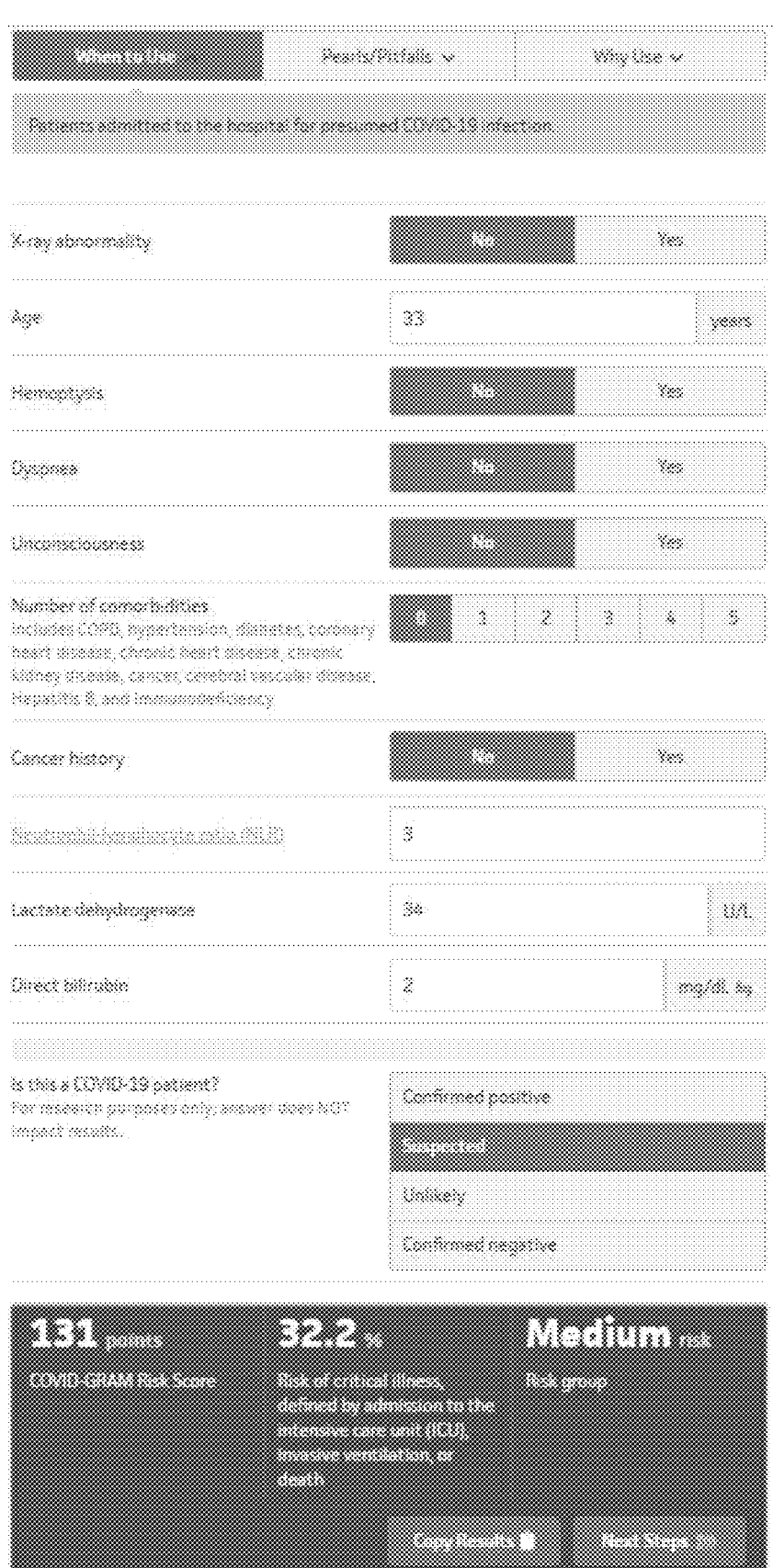

FIGS. 21A-21C illustrate an implementation of a mechanism to diagnose COVID-19 on a patient potentially or actually infected with COVID-19. In FIG. 21A, the mechanism assesses a severity of such a patient based on an age of the patient, an existence of an X-ray abnormality, hemoptysis, dyspnea, unconsciousness and cancer history, along with a number of comorbities, a neutrophil-lymphocyte ratio (NLR), lactate dehydrogenase, and direct bilirubin. FIG. 21B illustrates perils and pitfalls of the mechanism of FIG. 21A. FIG. 21C illustrates objectives or purposes of the mechanism of FIG. 21A.

FIG. 22 illustrates an implementation of a mechanism to diagnose COVID-19 on a patient potentially or actually infected with COVID-19. The mechanism illustrated in FIG. 22 determines a risk of critical illness at 24 hours based on a respiratory rate, pulse oximetry, and an O$_2$ flow rate of the patient.

The program code that enables the system to perform various search, display, calculation and other functions can be programmed in a manner that enables the deployment of the program in any computing system, including without limitation computer servers (e.g., on a web interface), personal computers, tablets, smart phones and smart watches.

When a user searches for or uses a diagnostic test, method, or protocol, prognostic method, algorithm, and/or determination of a treatment option, the system can recognize the medical service that user may potentially need. In this respect, the system can include information of medical service providers (e.g., doctors, hospital, healthcare consultants) and provide the information to relevant users and at an appropriate interface.

Information of medical service providers can be added to the system by administrators managing the system, but preferably added by the providers themselves. In one instance, each medical service provider is able to create an account on the system and add its contact, medical expertise, and location, without limitation. The creation of the account and addition of the information can be either controlled by a system administer, or automatically authorized given certain credential (e.g., email address) pre-approved by the system. For example, a user with an email address ending with @nyumc.org will be able to register as a medical professional or organization and add information related to New York University Medical Center.

In addition to adding the information of the medical service provider into the system, the provider can further associate such information to one or more diagnostic tests, methods, or protocols, prognostic methods, algorithms, and/ or determinations of treatment options. Therefore, when a user searches for diagnostic tests, methods, or protocols, prognostic methods, algorithms, and/or determinations of treatment options relating to "Chest Pain", in addition to displaying a list of diagnostic tests, methods, or protocols, prognostic methods, algorithms, and/or determinations of treatment options, the system also includes listing of medical service providers that have associated the services they provide to diseases causing chest pain.

In another example, during a search, when a user navigates to the interface displaying relevant tags or filters, the user will be able to see a list of medical service providers by clicking at a tag or filter. For instance, when the user clicks on "radiology", a list of radiologists (or medical service providers associating themselves to the filter "radiology") will be displayed along with the diagnostic tests, methods, or protocols, prognostic methods, algorithms, and/or determinations of treatment options.

The search and display can further be personalized based on a user's location or other characteristics. For instance, different medical service providers may be identified and listed depending on the age or gender of the user. In this respect, the user can opt to provide location, age or gender to the system, and the medical service providers need to annotate their service to certain location, age, and/or gender groups.

The techniques described herein, for example of the one or more processors 106, are implemented by one or more special-purpose computing devices. The special-purpose computing devices may be hard-wired to perform the techniques, or may include circuitry or digital electronic devices such as one or more application-specific integrated circuits (ASICs) or field programmable gate arrays (FPGAs) that are persistently programmed to perform the techniques, or may include one or more hardware processors programmed to perform the techniques pursuant to program instructions in firmware, memory, other storage, or a combination.

Figure 23:
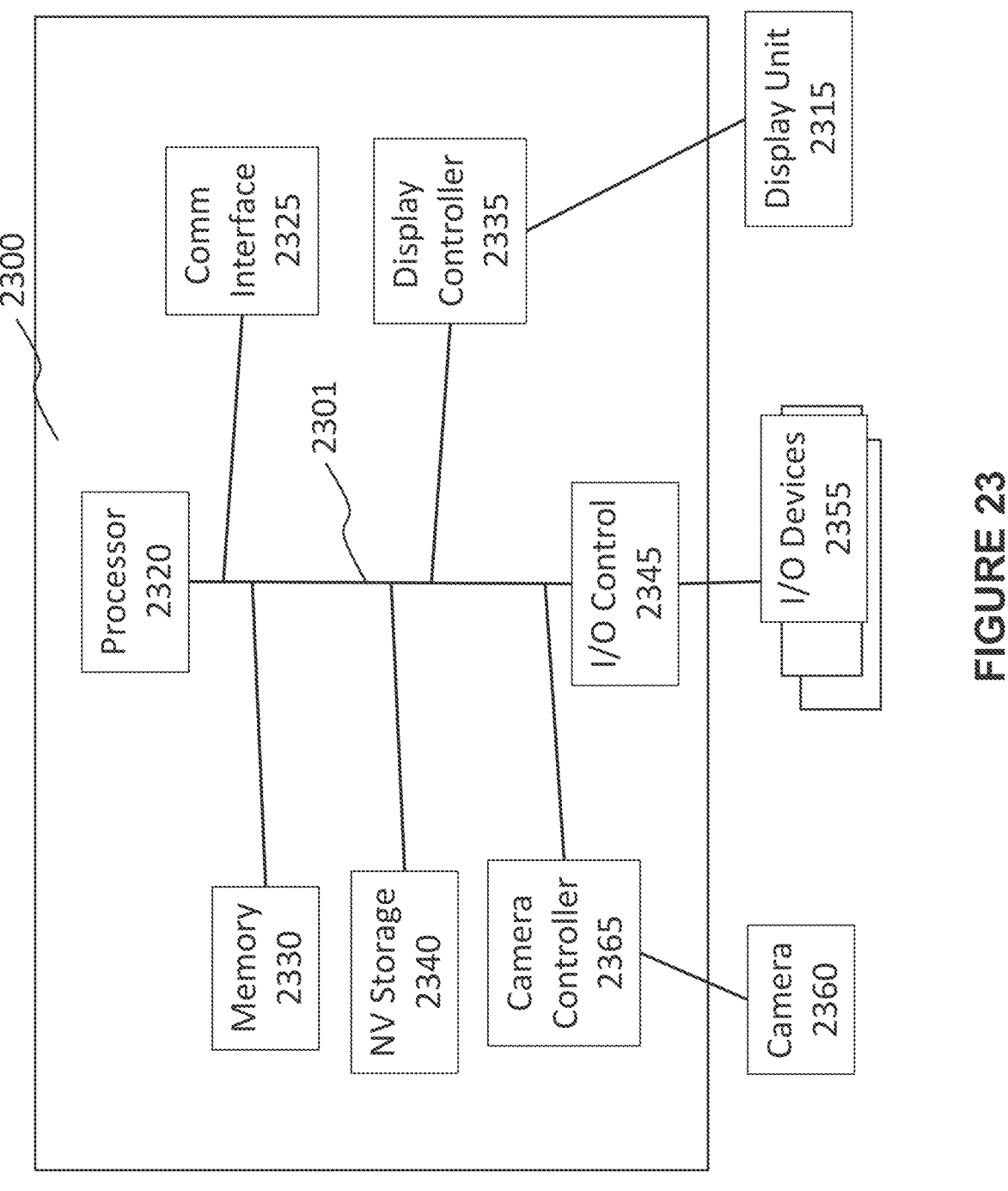
FIG. 23 illustrates a block diagram of a computer system upon which any of the embodiments described herein may be implemented.

FIG. 23 shows an example of a computer system 2300 on which techniques described in this paper can be implemented. The computer system 2300 can be used as a client computer system, such as a wireless client or a workstation, or a server computer system. The computer system 2300 includes a computer 2305, I/O devices 2355, and a display device 2315. The computer 2305 includes a processor 2320, a communications interface 2325, memory 2330, display controller 2335, camera controller 2365, non-volatile (NV) storage 2340, and I/O controller 2345. The computer 2305 may be coupled to or include the I/O devices 2355, camera 2360, and display unit 2315.

The computer 2305 interfaces to external systems through the communications interface 2325, which may include a modem or network interface. It will be appreciated that the communications interface 2325 can be considered to be part of the computer system 2300 or a part of the computer 2305. The communications interface 2325 can be an analog modem, ISDN modem, cable modem, token ring interface, satellite transmission interface (e.g. "direct PC"), or other interfaces for coupling a computer system to other computer systems.

The processor 2320 may be, for example, an Intel Pentium microprocessor or Motorola power PC microprocessor. The memory 2330 is coupled to the processor 2320 by a bus 2350. The memory 2330 can be Dynamic Random Access Memory (DRAM) and can also include Static RAM (SRAM). The bus 2350 couples the processor 2320 to the memory 2330, also to the non-volatile storage 2340, to the display controller 2335, and to the I/O controller 2345.

The I/O devices 2355 can include a keyboard, disk drives, printers, a scanner, and other input and output devices, including a mouse or other pointing device. The display controller 2335 may control a display on the display device 2315, which can be, for example, a cathode ray tube (CRT) or liquid crystal display (LCD).

The non-volatile storage 2340 is often a magnetic hard disk, an optical disk, or another form of storage for large amounts of data. Some of this data is often written, by a direct memory access process, into memory 2330 during execution of software in the computer 2305. One of skill in the art will immediately recognize that the terms "machine-readable medium" or "computer-readable medium" includes any type of storage device that is accessible by the processor 2320 and also encompasses a carrier wave that encodes a data signal.

The computer system 2300 is one example of many possible computer systems that have different architectures. For example, personal computers based on an Intel microprocessor often have multiple buses, one of which can be an I/O bus for the peripherals and one that directly connects the processor 2320 and the memory 2330 (often referred to as a memory bus). The buses are connected together through bridge components that perform any necessary translation due to differing bus protocols.

Network computers are another type of computer system that can be used in conjunction with the teachings provided herein. Network computers do not usually include a hard disk or other mass storage, and the executable programs are loaded from a network connection into the memory 2330 for execution by the processor 2320. A Web TV system, which is known in the art, is also considered to be a computer system, but it may lack some of the features shown in FIG. 23, such as certain input or output devices. A typical computer system will usually include at least a processor, memory, and a bus coupling the memory to the processor.

In general, a computer system will include a processor, memory, non-volatile storage, and an interface. A typical computer system will usually include at least a processor, memory, and a device (e.g., a bus) coupling the memory to the processor. The processor can be, for example, a general-purpose central processing unit (CPU), such as a microprocessor, or a special-purpose processor, such as a microcontroller. An example of a computer system is shown in FIG. 23.

The memory can include, by way of example but not limitation, random access memory (RAM), such as dynamic RAM (DRAM) and static RAM (SRAM). The memory can be local, remote, or distributed. As used in this paper, the term "computer-readable storage medium" is intended to include only physical media, such as memory. As used in this paper, a computer-readable medium is intended to include all mediums that are statutory, and to specifically exclude all mediums that are non-statutory in nature to the extent that the exclusion is necessary for a claim that includes the computer-readable medium to be valid. Known statutory computer-readable mediums include hardware (e.g., registers, random access memory (RAM), non-volatile (NV) storage, to name a few), but may or may not be limited to hardware.

The bus can also couple the processor to the non-volatile storage. The non-volatile storage is often a magnetic floppy or hard disk, a magnetic-optical disk, an optical disk, a read-only memory (ROM), such as a CD-ROM, EPROM, or EEPROM, a magnetic or optical card, or another form of storage for large amounts of data. Some of this data is often written, by a direct memory access process, into memory during execution of software on the computer system. The non-volatile storage can be local, remote, or distributed. The non-volatile storage is optional because systems can be created with all applicable data available in memory.

Software is typically stored in the non-volatile storage. Indeed, for large programs, it may not even be possible to store the entire program in the memory. Nevertheless, it should be understood that for software to run, if necessary, it is moved to a computer-readable location appropriate for processing, and for illustrative purposes, that location is referred to as the memory in this paper. Even when software is moved to the memory for execution, the processor will typically make use of hardware registers to store values associated with the software, and local cache that, ideally, serves to speed up execution. As used in this paper, a software program is assumed to be stored at an applicable known or convenient location (from non-volatile storage to hardware registers) when the software program is referred to as "implemented in a computer-readable storage medium." A processor is considered to be "configured to execute a program" when at least one value associated with the program is stored in a register readable by the processor. Thus, the processor may include software, hardware, and firmware.

In one example of operation, a computer system can be controlled by operating system software, which is a software program that includes a file management system, such as a disk operating system. One example of operating system software with associated file management system software is the family of operating systems known as Windows® from Microsoft Corporation of Redmond, Washington, and their associated file management systems. Another example of operating system software with its associated file management system software is the Linux operating system and its associated file management system. The file management system is typically stored in the non-volatile storage and causes the processor to execute the various acts required by the operating system to input and output data and to store data in the memory, including storing files on the non-volatile storage.

The bus can also couple the processor to the interface. The interface can include one or more input and/or output (I/O) devices. The I/O devices can include, by way of example but not limitation, a keyboard, a mouse or other pointing device, disk drives, printers, a scanner, and other I/O devices, including a display device. The display device can include, by way of example but not limitation, a cathode ray tube (CRT), liquid crystal display (LCD), or some other applicable known or convenient display device. The interface can include one or more of a modem or network interface. It will be appreciated that a modem or network interface can be considered to be part of the computer system. The interface can include an analog modem, Integrated Services Digital Network (ISDN) modem, cable modem, token ring interface, satellite transmission interface (e.g. "direct PC"), or other interfaces for coupling a computer system to other computer systems. Interfaces enable computer systems and other devices to be coupled together in a network.

Several components described in this paper, including clients, servers, and engines, can be compatible with or implemented using a cloud-based computing system. As used in this paper, a cloud-based computing system is a system that provides computing resources, software, and/or information to client devices by maintaining centralized services and resources that the client devices can access over a communication interface, such as a network. The cloud-based computing system can involve a subscription for services or use a utility pricing model. Users can access the protocols of the cloud-based computing system through a web browser or other container application located on their client device.

This paper describes techniques that those of skill in the art can implement in numerous ways. For instance, those of skill in the art can implement the techniques described in this paper using a process, an apparatus, a system, a composition of matter, a computer program product embodied on a computer-readable storage medium, and/or a processor, such as a processor configured to execute instructions stored on and/or provided by a memory coupled to the processor. Unless stated otherwise, a component such as a processor or a memory described as being configured to perform a task may be implemented as a general component that is configured to perform the task at a given time or a specific component that is manufactured to perform the task. As used in this paper, the term 'processor' refers to one or more devices, circuits, and/or processing cores configured to process data, such as computer program instructions.

A detailed description of one or more implementations of the invention is provided in this paper along with accompanying figures that illustrate the principles of the invention. The invention is described in connection with such implementations, but the invention is not limited to any implementation. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

Some portions of the detailed description are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of operations leading to a desired result. The operations are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

Techniques described in this paper relate to apparatus for performing the operations. The apparatus can be specially constructed for the required purposes, or it can comprise a general-purpose computer selectively activated or reconfigured by a computer program stored in the computer. Such a computer program may be stored in a computer-readable storage medium, such as, but is not limited to, read-only memories (ROMs), random access memories (RAMs), EPROMS, EEPROMs, magnetic or optical cards, any type of disk including floppy disks, optical disks, CD-ROMs, and magnetic-optical disks, or any type of media suitable for storing electronic instructions, and each coupled to a computer system bus.

Unless the context requires otherwise, throughout the present specification and claims, the word "comprise" and variations thereof, such as, "comprises" and "comprising" are to be construed in an open, inclusive sense, that is as "including, but not limited to." Recitation of numeric ranges of values throughout the specification is intended to serve as a shorthand notation of referring individually to each separate value falling within the range inclusive of the values defining the range, and each separate value is incorporated in the specification as it were individually recited herein. Additionally, the singular forms "a," "an" and "the" include plural referents unless the context clearly dictates otherwise. The phrases "at least one of," "at least one selected from the group of," or "at least one selected from the group consisting of," and the like are to be interpreted in the disjunctive (e.g., not to be interpreted as at least one of A and at least one of B).

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment, but may be in some instances. Furthermore, the particular features, structures, or characteristics may be combined in any suitable manner in one or more embodiment.

A component being implemented as another component may be construed as the component being operated in a same or similar manner as the another component, and/or comprising same or similar features, characteristics, and parameters as the another component.

The invention claimed is:

1. A method of improving medical diagnosis, prognosis, or treatment, comprising:

accessing a digital health record, wherein the digital health record comprises windows corresponding to different categories of information;

identifying, from the digital health record, an entry in which a replacement string or an additional string is to be suggested, based on an ambiguity of the entry or an inconsistency or a conflict with other data in the digital health record;

obtaining a first training set that comprises first suggestions that are accepted as being viable replacements or additions to the existing text;

obtaining a second training set that comprises second suggestions that are rejected as being nonviable replacements or additions to the existing text;

training one or more machine learning models using the first training set and the second training set;

predicting, by the one or more machine learning models, a particular string to suggest as a replacement or addition to existing text in the entry and one or more alternatives to the particular string based on respective probabilities of veracity of the particular string and the one or more alternatives;

in response to suggesting the particular string, presenting sources of data within the digital health record that support the particular string and the one or more alternatives to the particular string, wherein the sources of data correspond to one or more of the windows;

receiving an input, the input indicating whether the particular string or the one or more alternatives are accepted, or including a manually inputted string that is distinct from the particular string and the one or more alternatives;

updating the entry based on the received input;

determining or inferring any particular emphasis or any particular bias of the input towards a particular window of the digital health record over other windows of the digital health record;

training the one or more machine learning models according to the any particular emphasis or any particular bias;

determining a presence of a particular medical condition based on semantic segmentation and instance segmentation to determine first boundaries between different tissue types and second boundaries between common tissue types;

determining, based on the presence of the particular medical condition, a surgery to be implemented, the one or more machine learning models being trained according to particular medical conditions and particular measures to be implemented;

presenting, as an overlay over an existing window or a sidebar at a side of the existing window, a suggestion of the surgery;

receiving an acceptance of the suggestion of the surgery;

presenting a prompt to select a surgical machine associated with the surgery;

receiving an acceptance of the surgical machine;

following execution of a protocol by the surgical machine, receiving, from the surgical machine, a result associated with the execution; and updating a portion of the digital health record according to the result.

2. The method of claim 1, wherein the determining a particular string to suggest comprises determining a particular string indicating a COVID-19 status of a patient, the COVID-19 status being determined based on whether a patient has breathing or speech difficulties, a respiratory rate, a $PaO_2$ and $SpO_2$ level, and an analysis of a chest X-ray of the patient.

3. The method of claim 1, further comprising:

receiving a textual input into the entry; and wherein the determining the particular string to suggest is simultaneous with the receiving of the textual input.

4. The method of claim 1, wherein the determining the particular string is based on a context of the entry.

5. The method of claim 1, wherein the digital health record comprises a problem list including one or more illnesses, one or more injuries, and one or more risk factors and a medication list including one or more drugs and one or more prescribed respective dosages; and the determining the particular string is based on an item in the problem list and an item in the medication list.

6. The method of claim 1, further comprising:

identifying other entries in the digital health record to be updated based on the input.

7. The method of claim 1, wherein the presenting one or more alternatives to the particular string is in a drop-down list that enables switching between selection of the particular string or the one or more alternatives.

8. The method of claim 1, further comprising presenting a confidence level indicating a probability of relevance of the particular string.

9. The method of claim 8, further comprising presenting confidence levels indicating one or more probabilities of relevance of each of the one or more alternatives.

10. The method of claim 1, wherein the determining a particular string comprises importing a calculation of a parameter.

11. The method of claim 10, wherein:

the particular string comprises a dot-phrase or a native macro; and the input indicates that the particular string is accepted; and the method further comprises:

populating a chart based on the input.

12. The method of claim 1, wherein, in response to receiving the input to override the particular string and the one or more alternatives, determining that the entry is to be maintained.

13. The method of claim 1, wherein:

the identifying an entry in which a replacement string or an additional string is to be suggested comprises identifying a numeral that is missing a subsequent unit of measurement.

14. The method of claim 13, wherein:

the determining a particular string to suggest comprises determining a particular unit of measurement to append to the numeral based on the context of the entry.

15. The method of claim 1, further comprising identifying a type of the received input; and wherein the determining a particular string to suggest is based on the one or more machine learning models being trained by a feedback mechanism taking into account the type of the received input.

16. The method of claim 12, further comprising:

identifying a frequency at which the received input or the one or more alternatives is selected; and wherein the determining a particular string to suggest is based on the one or more machine learning models being trained by a feedback mechanism taking into account the type of the received input.

17. The method of claim 1, further comprising:

identifying data in the entry having a reliability below a threshold; and flagging the data.

18. The method of claim 17, wherein the identifying data in the entry having a reliability below a threshold comprises detecting data having a source other than a sensor reading or a calculation of a parameter.

19. The method of claim 1, further comprising presenting one or more respective sources of the one or more alternatives to the particular string.

20. The method of claim 1, wherein the identifying, from the digital health record, an entry comprises:

identifying a plurality of entries of which at least one of the entries conflicts or contradicts other entries; and determining which of the entries is more likely to be inaccurate compared to another of the entries.

* * * * *